United States Patent [19]

Coben

[11] Patent Number: 4,528,627
[45] Date of Patent: Jul. 9, 1985

[54] METHOD FOR CEPHALOMETRIC QUANTITATION AND EXPRESSION OF GROWTH

[76] Inventor: Eugene S. Coben, 956 Coates Rd., Meadowbrook, Pa. 19046

[21] Appl. No.: 441,283

[22] Filed: Nov. 12, 1982

[51] Int. Cl.³ .............................................. G06G 7/60
[52] U.S. Cl. .................................... 364/415; 433/69; 433/68; 128/77
[58] Field of Search ...................... 364/415, 413, 414; 378/162–166, 205, 206; 128/777, 749; 433/69, 68

[56] References Cited

U.S. PATENT DOCUMENTS

| | | | |
|---|---|---|---|
| 2,254,544 | 9/1941 | Plotz et al. | 378/205 |
| 3,996,666 | 12/1976 | Blanque | 128/777 |
| 4,197,855 | 4/1980 | Lewin | 364/415 |
| 4,386,405 | 5/1983 | Lewin et al. | 364/415 |
| 4,400,819 | 8/1983 | Bens et al. | 378/163 |

Primary Examiner—Jerry Smith
Assistant Examiner—Michael R. Fleming

[57] ABSTRACT

A method for cephalometric quantitation of the morphology and growth of a patient is provided comprising the steps of making a lateral cephalometric X-ray of the patient, registering an X-ray with the analyzer, registering anatomic landmarks to determine coordinates of cephalometric readings sought to be quantified with said analyzer, summating the linear size, proportion and angular relationship of variants comprising the cephalometric regions and recording of results of the summating step for future reference. The method identifies areas of facial disharmony and quantifies the degree of change in the surgical repositioning of dento-facial structures. The analyzer used in the present invention can comprise a computer which permits instantaneous summation and therefore instant comparative analysis for purposes of treatment.

10 Claims, 9 Drawing Figures

CRANIAL BASE

BASION HORIZONTAL
COBEN COORDINATE ANALYSIS

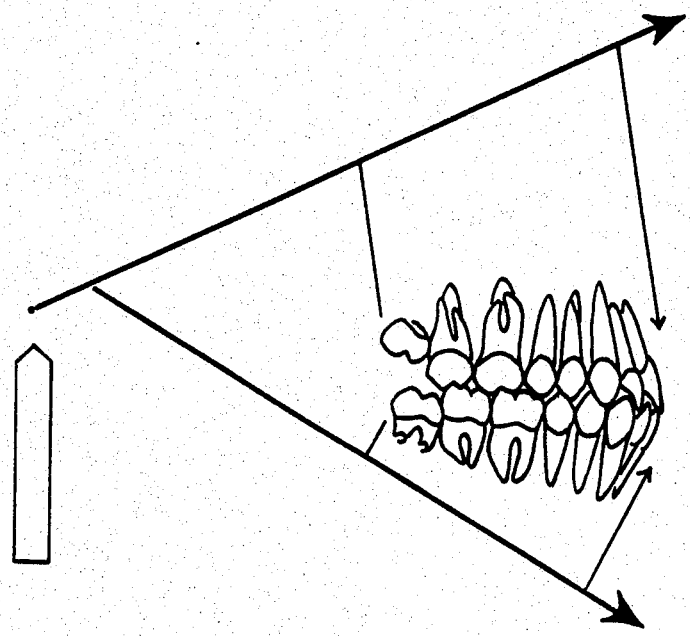

Fig. 1 General vectors of craniofacial growth. Growth of the cranial base translates the upper face and the maxillary dentition upward and forward away from the foramen magnum. Growth of the mandible translates the lower dentition downward and forward. The two diverging vectors create space for vertical facial development and tooth eruption. (Coben, Angle Ortho. 1961)

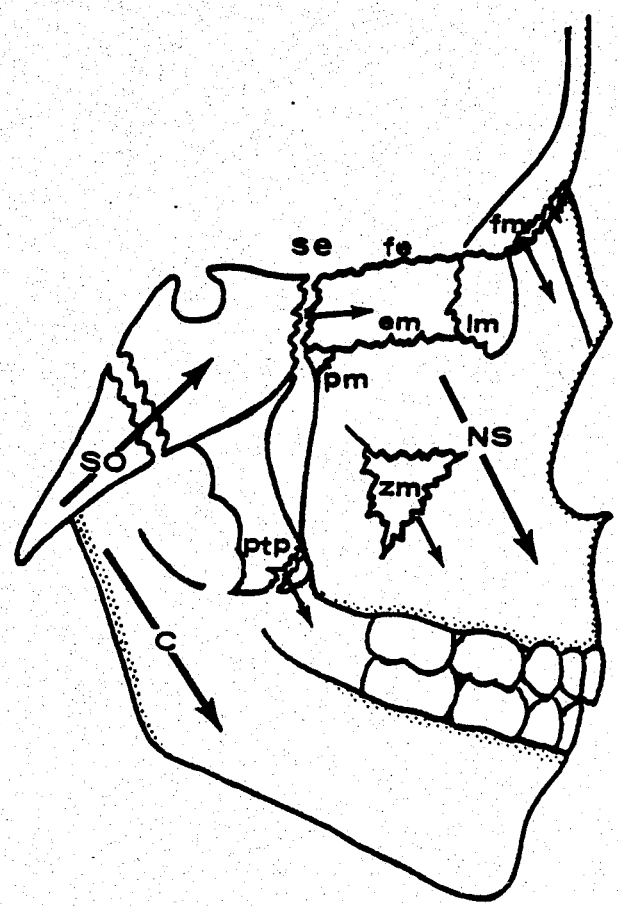

Fig. 2 Postnatal craniofacial growth systems to the age of 7 years (first decade). Cartilaginous growth: SO, Spheno-occipital synchondrosis; C, reflection of condylar mandibular growth; NS, nasal septum. Spheno-ethmoidal circum-maxillary suture system: se, Spheno-ethmoidal; ptp, pterygopalatine; pm, palatomaxillary; fe, fronto-ethmoidal; em, ethmoidal-maxillary; lm, lacrymal-maxillary; fm, frontomaxillary; zm, zygomaticomaxillary; zt, zygomaticotemporal (not shown). Surface apposition- modeling resorption development (stippled area): minor contribution. (Coben, A.J.O. 1966)

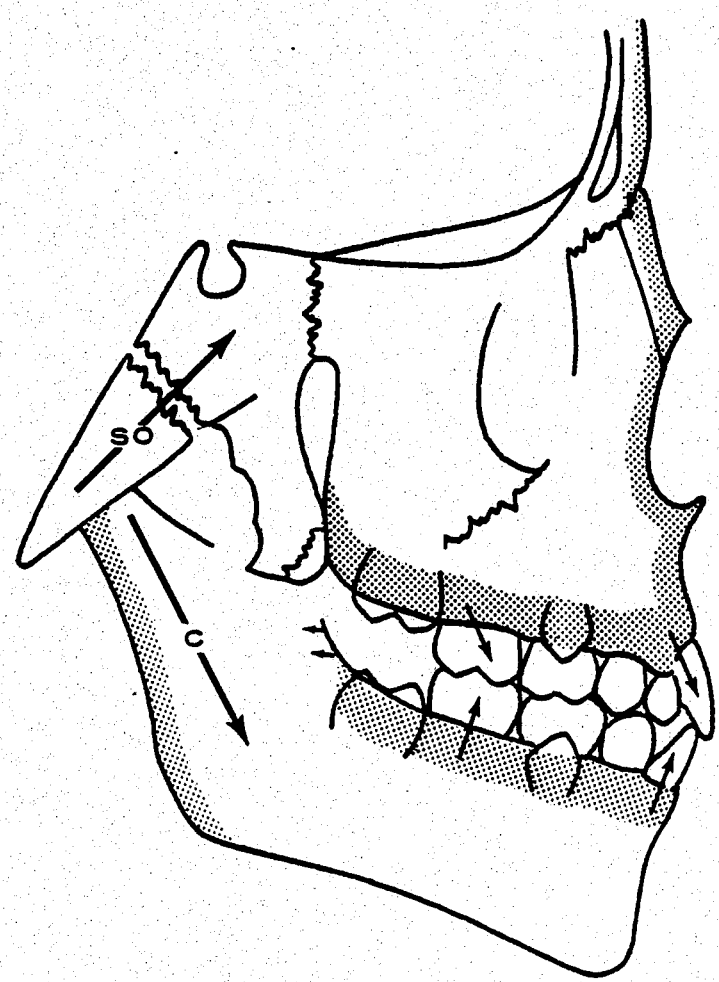

Fig. 3 Postnatal craniofacial growth systems from age 7 (second decade). Cartilaginous growth: SO, Spheno-occipital synchondrosis --- active through puberty; C, reflection of condylar mandibular growth --- active to facial maturity; nasal septum --- growth completed. Spheno-ethmoidal circummaxillary suture system: Sutural growth no longer primary system of upper facial development. Surface apposition-modeling resorption development (stippled area): Now major method of upper facial development and alveolar growth. (Coben, A.J.O. 1966)

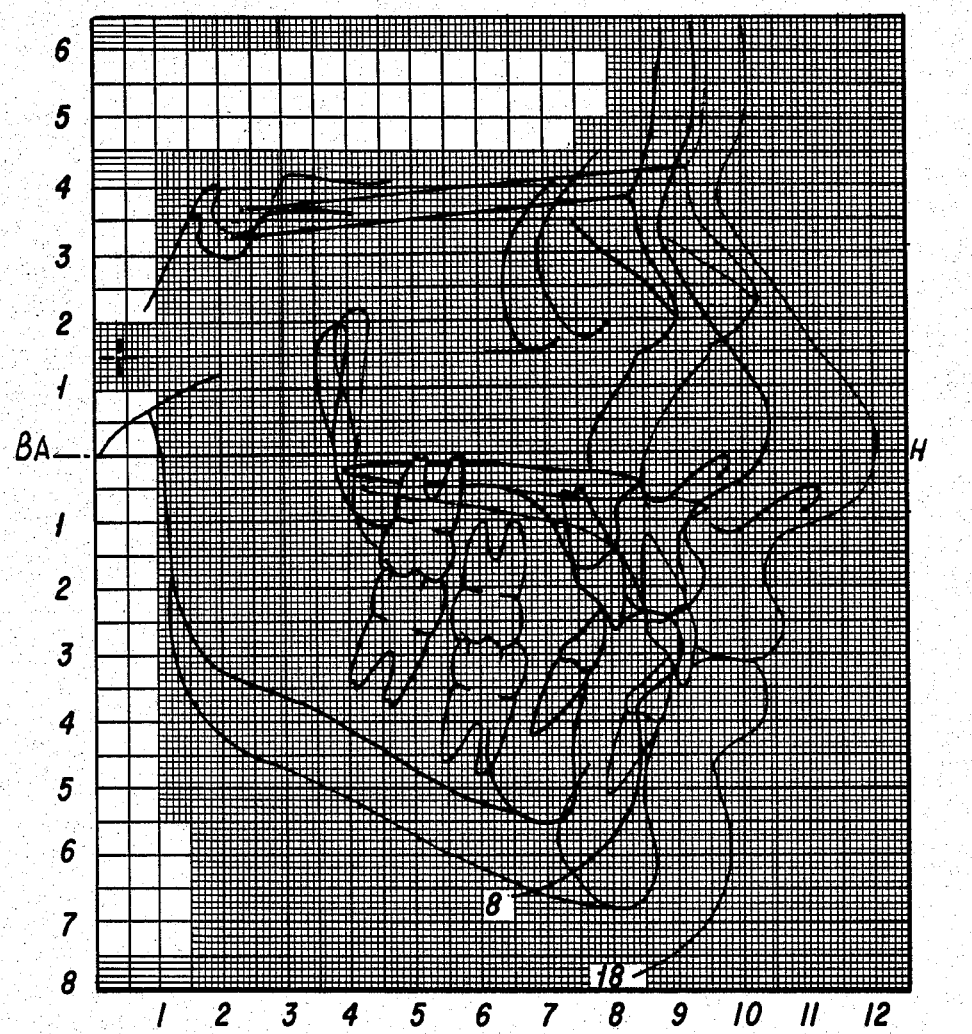
Fig. 4  Basion Horizontal Coordinate Tracing Film.
Coben Coordinate Analysis

BASION HORIZONTAL
COBEN COORDINATE ANALYSIS

Fig. 6.   BASION HORIZONTAL
COBEN COORDINATE ANALYSIS

**BASION HORIZONTAL
COBEN COORDINATE ANALYSIS**

BASION HORIZONTAL

COBEN COORDINATE ANALYSIS

BASION HORIZONTAL
COBEN COORDINATE ANALYSIS

METHOD FOR CEPHALOMETRIC QUANTITATION AND EXPRESSION OF GROWTH

FIELD OF THE INVENTION

The present invention is directed to a method which integrates craniofacial growth with a system for its quantitative analysis. More specifically, the present invention is directed to a synthesized integrated approach to craniofacial growth and treatment in that the cephalometric quantitative anlyasis measures and expresses such growth. Even more specifically, a method of tabulating and graphically illustrating such growth is also provided. The method graphically illustrates the quantitative analysis and its integration with therapeutic programs reflecting a total concept of growth and measurement applicable to various fields including orthodontics and maxillo-facial surgery. Even more specifically, various portions of the method are computerized.

BACKGROUND AND PRIOR ART STATEMENT

Much of contemporary cephalometric methodology represents a confusion of dichotomies made up of conflicting concepts of craniofacial growth, unlimited systems of quantitation, contradictory methods of superimposing tracings, all generally unrelated to each other and perpetuated merely by tradition. What has occurred is that major clinical treatment rationales have been built upon erroneous concepts.

The time has long passed when the number of quantitative systems were limited only by the number of points, planes and geometric combinations one could devise. Gone are the days when the ever pressing goal was the discovery of some elusive statistically significant correlation of measurements, irrespective of their biologic rhyme or reason. Those who have lived with this tool in research and tried to apply cephalometrics to clinical practice have come to view such approaches with skepticism and criticism. All too often the philosophy was an outgrowth of a system of quantitation when in reality, the systems should have quantitated the philosophy. In this light, the method of the present invention, Basion Horizontal, is presented as a coherent interrelated concept which in its broadest sense is a totally integrated philosophy of orthodontic rationale.

The basic concept of the present invention was introduced in a serial growth study published in 1955 under the title "The Integration of Facial Skeletal Variants" by S. E. Coben, Am. J. Orthod 41: 407–434. In this publication, the concept of Basion Horizontal (BaH) was introduced and defined as the plane parallel to the Frankfort horizontal plane whose point of origin is Basion. As such, Basion Horizontal represents the foramen magnum plane of orientation. The craniofacial growth concept which Basion Horizontal represents was indicated in 1961 to be that growth of the cranial base and growth of the mandible as reflected away from the foramen magnum (Basion) and the vertebral column. "Growth Concepts", by S. E. Coben, Angle Orthod. 31: 194-201, 1961. The craniomaxillary complex housing the maxillary dentition is translated upward and forward away from Basion by cranial base growth whereas mandibular growth carries the mandibular dentition downward and forward (FIG. 1). The divergence of the two general vectors creates space for vertical facial development and eruption of the dentition. In 1966 these vectors were related to systems of craniofacial growth. "Growth and Class II Treatment", by S. E. Coben, Am. J. Orthod. 52: 5-26, 1966. See FIGS. 2 and 3. The cranial base vector represents the upward and forward spatial translation of the upper face by growth of the spheno-occipital synchrondosis as growth of the spheno-ethmoidal circum-maxillary suture system and the nasal septum increase the depth and height of the upper face. Because the mandible maintains a constant spatial relation to the foramen magnum, the lower face vector represents the total reflection of mandibular growth carrying the lower teeth downward and forward away from the cranial base.

In 1966 it was suggested that two growth illustrations were necessary because of the two distinct phases of craniofacial growth created by a change in the system of upper facial development after the approximate age of seven. Prior to age seven, growth of the upper face is dominated by the nasal septum, the eyeballs, and the spheno-ethmoidal circum-maxillary suture system which creates space for the erupting maxillary molars. Bone apposition and remodeling resorption appears to be a minor secondary growth system at this time. At the age of seven, the growth system of the upper face changes with the closure of the spheno-ethmoidal suture. After the age of seven, the sella-frontale dimension stabilizes whereas the thickness of the frontal bone begins to increase by surface apposition and remodeling until maturity. The interpretation is that after the age of seven, the primary system of spheno-ethmoidal circum-maxillary sutural growth of the upper face is replaced by a primary system of surface apposition and remodeling resorption. Prior to age seven, space for the erupting upper molars is created by growth of the spheno-ethmoidal circum-maxillary suture system. After the age of seven, space must be created for the upper 2nd and 3rd molars by maxillary alveolar apposition as the maxillary molars erupt downward and forward to create retromolar space.

In 1979 a coordinate tracing film was suggested to express the growth concept both quantitatively and graphically. "Basion Horizontal Coordinate Tracing Film", by S. E. Coben, Am. J. Orthod. 13: 598-605, 1979. See FIG. 4. The coordinate grid was enlarged 8% to compensate for a standard cephalometric X-ray enlargement of 8%.

SUMMARY OF THE PRESENT INVENTION

The present invention provides for the first time an entire method for the cephalometric quantitation and expression of growth of a patient. The cephalometric regions for reflecting the method quantify and express growth by summating the linear size, proportions and angular relationships of variants of the present invention for the cephalometric regions to be quantified which include the cranial base, facial depth, facial height, dentition, and profile.

A lateral X-ray representing the midsagittal plane of a patient is taken. An analyzer is registered with the X-ray in a manner which orients it with an anatomic landmark, Basion, such that the horizontal components of the analyzer parallel the X-ray Frankfort Horizontal plane of the lateral X-ray. Variants of the present invention comprise specific anatomical landmarks which are in-putted using the analyzer to determine the coordinates of each landmark. The variants are summated and preferably recorded. A data base quantifying mean and standard deviation values for the variants at given patient ages are available for comparative purposes.

In one embodiment serial lateral X-rays of the patient are taken over various time intervals and the variants with respect to the cephalometric analysis for each X-ray are summated and recorded. The variants are compared indicating areas of growth. This data can be utilized by the clinician during the treatment of the patient. Serial tracings and/or replications of the lateral X-rays may be superimposed or graphically illustrated (by computer) for formulating therapeutic stratagem.

Other aspects of the present invention will become apparent from a reading of the Detailed Description of The Preferred Embodiment, The Drawing Figures, The Examples, and The Claims.

DRAWING FIGURES

FIG. 1 represents the basic concept illustrating general vectors of craniofacial growth as taught by the inventor in 1961.

FIG. 2 represents postnatal craniofacial growth systems for the first decade as taught by the inventor in 1966.

FIG. 3 represents postnatal craniofacial growth systems for the second decade as taught by the inventor in 1966.

FIG. 4 represents tracing film developed by the inventor and taught in 1979.

DETAILED DESCRIPTION OF THE PREFERRED EMBODIMENT

Figure 5:
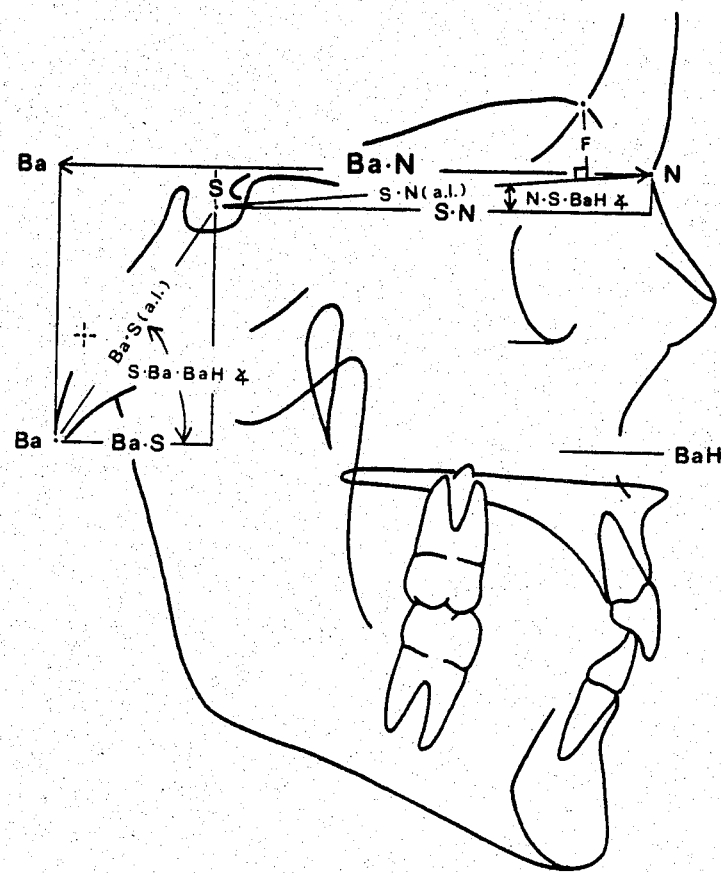
FIG. 5 depicts variants and anatomical landmarks used in the method of the present invention for the cranial base.

The present invention expresses a growth philosophy by using a rectangular coordinate system wherein the reference abscissa is Basion Horizontal (BaH) and the point of "zero" registration for both horizontal and vertical measurements is Basion (Ba). Measurements of facial depth are the expression of the horizontal component of growth vectors contributing to the forward development of the face relative to the foramen magnum. Similarly, increments of facial height are vertically related to the foramen magnum, measured as the expression of the vertical component of growth vectors contributing to the height of the face. Facial depth is measured along abscissas parallel to BaH; facial height is measured along ordinates, termed Basion Vertical (BaV), perpendicular to BaH. The rectangular coordinate system permits measurement of the linear size of craniofacial segments and, by a system of proportions, evaluates the skeletal proportionality which results in the individual profile type. This constitutes a morphologic evaluation; however, more important is the use of this method for the analysis of growth and tooth movement during surgical treatment including orthodontics.

In a growth analysis, the linear increment of each segment of the craniofacial pattern is measured and mathematically summated to quantitate its cumulative effect on the spatial position of the dentition and its effect on the form of the skeletal and soft tissue profiles.

Cephalometric X-rays are taken consistent with the foregoing and an analyzer which reduces all measurements to absolute values is positioned to read the X-ray films with the "Ba" of the grid registered on anatomic Basion and oriented with horizontal coordinates parallel to Frankfort horizontal (FH). In the preferred embodiment, the analyzer is a computer having a digitizer as is known in the art. Anatomical landmarks and coordinates consistent with the present invention, are identified and measurements using such landmarks are read directly for growth assessment or when an interpretive evaluation is desired, the complete anatomical coordinate craniofacial, dentition and profile measurements are tabulated. Serial tracings and/or graphic illustrations may be made and comparison measurements and coordinate analyses tabulated generating comparative data indicating areas of growth. The comparative data may be utilized by the clinician in treatment. The method of the present invention quantitatively interrelates cranial base, face depth, face height, dentition, and profile into a complete craniofacial growth analysis. The relationship between the postual position of the head, the visual axis of the eye and the anterior cranial base does not change, and thus serial tracings employ a common SN/FH angular relationship and should be superimposed with SN and FH planes parallel. The Sella-Nasion (SN) plane is that which is drawn from Sella (S) to Nasion(N) representing the anterior cranial base. Thus, each subsequent coordinate tracing may be superimposed. In lieu of generation of computer graphics displaying the tracings, tracing film as depicted in FIG. 4 may be employed.

The method of the present invention quantifies and expresses the complete cephalometric growth by analyzing five regions; namely: cranial base, face depth, face height, dentition and profile. Although each are diagrammed and discussed separately, it must be stressed that they are completely interrelated quantitatively.

Cranial Base

The spatial position of the upper face and the maxillary dentition is not only dependent upon its growth and tooth eruption, but also upon the size and growth of the cranial base to which it is attached. Therefore, the analysis of the present invention quantitatively fractionates the linear size, angulation, and postural position of the posterior and anterior cranial base, summating their contribution to the overall depth and height of the upper face (FIG. 5, Example I).

Basion-Nasion (Ba.N), termed the total effective depth of the cranial base, is subdivided into the depth contribution of the posterior cranial base, Basion-Sella (Ba.S), and the depth contribution of the anterior cranial base, Sella-Nasion (S.N).

The effective depth of the posterior cranial base (Ba.S) varies with the absolute length (a.l.) of the posterior cranial base (Ba.S a.l.) and the inclination of the posterior cranial base in the pattern, as measured by its angular relation to Basion Horizontal (S.Ba.BaH∡), termed the Ba.S∡. The more horizontal the inclination of the posterior cranial base, the more its size and growth contributes to craniofacial depth (b=c cos A);

the more vertical, the more it contributes to height (a=c sin A). It is this measurement which reflects the increment and direction of growth of the spheno-occipital synchrondrosis.

The same method is employed in the analysis of the effective depth of the anterior cranial base (S.N). The effective depth of the anterior cranial base varies with the absolute length of the anterior cranial base (S.N a.l.) and the inclination of the anterior cranial base in the pattern, as measured by its angular relation to Basion Horizontal (N.S. BaH $\measuredangle$), termed the S.N$\measuredangle$.

Because the growth process of the anterior cranial base changes after age seven, the absolute length Sella-Nasion (S.N a.l.) is subdivided into that segment which cephalometrically can be considered as most closely representing the true anterior cranial base, and that segment which represents the thickness of the frontal bone. Anatomically, the limits of the anterior cranial base would be the pituitary fossa to the foramen caecum. Because the foramen caecum cannot be identified in the lateral X-ray film, a substitute cephalometric landmark, "frontale", is employed and is defined as the midpoint between the images of the superior orbital plates where they cross the image of the inner plate of the frontal bone. The frontale landmark is projected to the S-N plane by a perpendicular drawn from frontale to the S-N plane, the point of intersection designated as constructed Frontale (F). Thus, Sella-Frontale (S.F a.l.) is the cephalometric equivalent of the true anterior cranial base and Frontale-Nasion (F.N a.l.), the thickness of the frontal bone. Until the approximate age of seven, the Sella-Nasion (S.N a.l.) dimension increases in the Sella-Frontale (S.F a.l.) segment by growth of the spheno-ethmoidal suture whereas little increase in the thickness of the frontal bone (F.N a.l.) is noted. With closure of the spheno-ethmoidal suture at age seven, the Sella-Frontale (S.F a.l.) segment stabilizes, showing little additional increment, and the frontal bone (F.N a.l.) begins to increase in thickness by surface apposition and remodeling.

The effect of the Sella cranial base angle (S$\measuredangle$) is represented in the measurement of the posterior and anterior cranial base angles. When one measures the posterior cranial base angle, Sella-Basion-BaH angle (Ba.S$\measuredangle$), and the anterior cranial base angle, Nasion-Sella-BaH angle (S.N$\measuredangle$), what is being measured is the combined effect of the cranial base angle and the postural position of the head on the effective depth and height of the total cranial base, Basion-Nasion (Ba.N). The interrelationship of these variables is expressed by the equation: S$\measuredangle$=180°+(S.N$\measuredangle$)−Ba.S$\measuredangle$ Thus, the total effective depth of the cranial base, Basion to Nasion, is the summation of the effective depth of the posterior and anterior cranial bases and their respective variables. Measurements are summated and recorded in the Cranial Base segment of the Craniofacial Analysis. See Example I.

Facial Depth

Figure 6:
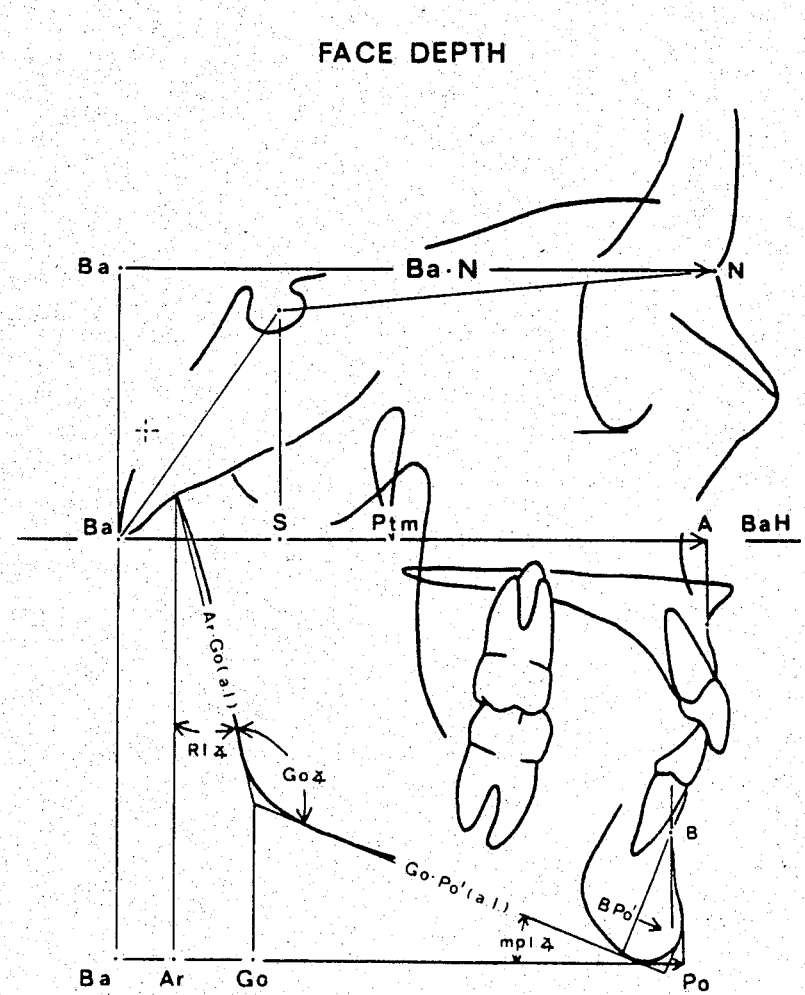
FIG. 6 depicts variants and anatomical landmarks used in the method of the present invention for the facial depth.

Mid-face depth is measured in the same manner, parallel to Basion Horizontal from Basion to Point "A". Point A (Subspinale) is the deepest midline point on the maxilla between the anterior nasal spine and prosthion (FIG. 6, Example I). The total effective mid-face depth (Ba.A) is fractioned by summating the effective depth contribution of the posterior cranial base (Ba.S), the depth contribution of the pterygoid plates measured from Sella to Ptm (S.Ptm) and the depth of the maxilla from Ptm to Point "A" (Ptm.A). Ptm or the pterygomaxillary fissure, is the point of intersection of the images of the anterior surface of the pterygoid process of the sphenoid bone and the posterior margin of the maxilla. The linear size of each of these dimensions is measured and its effect on the total mid-face depth is summated by simple addition. To express proportionality, that is to say whether a dimension is proportionally small or large for a face, each linear measurement is converted into a percentage of the total cranial base depth (% Ba.N). Measurements of mid-face depth are illustrated in FIG. 6 and recorded in the Facial Depth segment of the Craniofacial Analysis. See Example I.

Lower face depth is evaluated in a similar manner. The total effective depth of the lower face is measured from Basion to Pogonion (Ba.Po); Pognion being the most anterior midline point of the mandibular symphysis. The resultant effect of contributing variants is then determined and summated. Basion-Articulare, the latter of which is the point of intersection of the images of the posterior border of the condyle of the mandible in the inferior border of the basilar part of the occipital bone (Ba.Ar), represents the anteroposterior position of the mandible in the cranial base relative to Basion. Articulare to Pogonion (Ar.Po) is the effective contribution of the mandible to lower face depth. Basion to Point "B" (Ba.B), the latter of which is the deepest midline point on mandibular symphsis between infradentale and pognion is the mandibular apical base depth relative to Basion, expressed as the effective depth of the lower face less the effective depth of the chin (Ba.Po−B.Po).

Like the analysis of the cranial base, the effective depth contribution of the mandible (Ar.Po) is dependent upon the mandibular size, form and position in the pattern. In this determination, the depth contribution of the mandible is divided into the effective depth contribution of the ramus inclination, Articular-Gonion (Ar.Go), and the effective depth contribution of the mandibular body, Gonion-Pogonion (Go.Po). Gonion is the point formed by the intersection of the ramus plane and the mandibular plane. Each segment is then analyzed as was done in the cranial base.

The effective depth of the ramus inclination (Ar.Go) represents the resultant effect of the absolute length of the ramus as measured along its posterior border from Articulare to Gonion (Ar.Go a.l.) and the inclination of the ramus plane in the pattern, termed the Ramus Inclination Angle (RI$\measuredangle$). RPL, the ramus plane, is the plane drawn from articulare tangent to the most posterior inferior border of the ramus. The RI$\measuredangle$ is expressed relative to the BaV ordinate as the degree of deviation of the ramus plane from a vertical, or 90° relation, to Basion Horizontal (Ba.H). A forward inclination of the ramus plane is read as a positive or plus value; a posterior inclination is read as a negative or minus value. The greater the RI$\measuredangle$, meaning the more forward the ramus is inclined, the more the size and growth of the ramus contributes to the effective depth of the lower face (b=c sin B). Conversely, the smaller the RI$\measuredangle$, meaning a more vertical inclination of the ramus, the less the ramus size and growth contributes to lower face depth. Should the RI$\measuredangle$ be negative, additional ramus growth would make the chin point more retrognathic by decreasing the effective depth of the lower face.

The depth contribution of the mandibular body (Go.Po) varies with the absolute length of the mandibular body (Go.Po a.l.) and the mandibular plane angle (MPl$\measuredangle$). MPl is the angle formed by the mandibular plane and the BaH abscissa (FH) representing the inclination of the lower mandibular border in the pattern. The smaller the mandibular plane angle, the more the mandibular body size and growth contributes to lower face depth (b=c cos A). The larger the mandibular plane angle, the less mandibular body size and growth contributes to lower face depth and the more it contributes to lower face height.

B.Po′ is the anatomic chin, the position of the mandibular apical base relative to the corpus chin point, measured as an absolute length along the mandibular plane by projecting perpendiculars from the mandibular plane to point "B" and tangent to the most prominent point on the curvature of the mandibular symphysis (Po′). B.Po is the effective depth of the chin measured as the difference between the mandibular apical base Point "B" ordinate and the chin point Pogonion ordinate (BaV). The difference between the anatomic chin (B.Po′) and the effective depth of the chin (B.Po) is a function of the mandibular plane angle. As the mandibular plane angle approaches 0°, the effective depth of the chin (B.Po) begins to equal the absolute chin (B.Po′). Conversely, as the mandibular plane angle increases, the effective depth of the chin decreases to zero or even a negative value with Pogonion posterior to Point "B".

Like the cranial base angle, the effect of the Gonial Angle (Go∡) on the mandibular contribution to the depth and height of the lower face is evaluated in the measurement of the RI angle and the mandibular plane angle. The RI angle and the mandibular plane angle measure the resultant effect of both the gonial angle and the spatial position of the mandible in the pattern, as expressed in the equation: (Go∡)=RI∡+MPl∡+90°).

Facial Height

Figure 7:
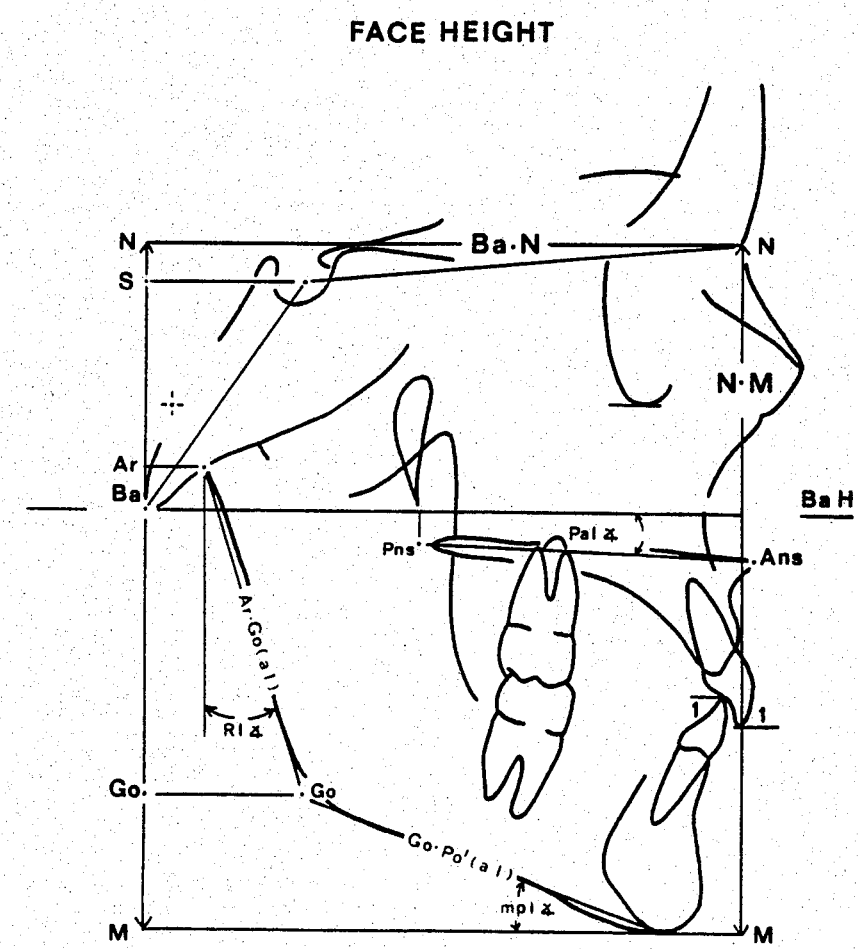
FIG. 7 depicts variants and anatomical landmarks used in the method of the present invention for the facial height.

To comprehend development of facial height, one must view the total anterior face height (N.M) as the vertical resultant of the divergence of the cranial base growth vector and the mandibular growth vector. Growth of the cranial base carries the upper face and maxillary dentition upward and forward away from the foramen magnum; mandibular growth carries the mandibular teeth downward and forward from the foramen magnum. Between the two divergent vectors, space is created for vertical development of the upper face, remodeling of the palate, and tooth eruption. Viewed in the context of this concept, the same quantitative system employed to fractionate the horizontal components of craniofacial growth is applied to vertical facial development (FIG. 7, Example I).

As such, total anterior face height measured from Nasion to Menton (N.M) is evaluated by summating the vertical expression of cranial base growth relative to Basion, Basion-Nasion (Ba.N), and the vertical expression of mandibular growth relative to Basion, Basion-Menton (Ba.M). Menton is the most inferior midline point on the mandibular symphysis. The total effective height of the cranial base contributing to upper face height, Basion-Nasion (Ba.N), is the summation of the effective height of the posterior cranial base, Basion-Sella (Ba.S), and the effective height of the anterior cranial base, Sella-Nasion (S.N). As previously and similarly defined, the effective heights of the posterior and anterior cranial bases are the resultants of their absolute lengths, Ba.S a.l. and S.N.a.l., and their inclination in the pattern as measured by the Ba.S∡ and the S.N.∡, respectively.

The expression of lower face height, Basion Menton (Ba. M), is evaluated by the summation of the effective lower posterior face height, Basion-Gonion (Ba.Go), and the effective mandibular corpus height, Gonion-Menton (Go.M). Lower posterior face height, Basion-Gonion (Ba.Go), is the resultant effective height equal to the effective height of the ramus, Articulare-Gonion (Ar.Go), less the superior position of Articulare relative to Basion (Ba.Ar). As in the depth analysis, the effective height of the ramus, Articulare-Gonion (Ar.Go), is a function of its absolute length (Ar.Go a.l.) and the inclination of the ramus plane in the pattern (RI∡). The smaller the RI∡, indicating a more vertically inclined ramus plane, the more ramal length and growth will contribute to the effective height of the lower face and the less to depth (a=c cos B). When the RI∡ is 0°, ramal growth is reflected solely in an increase in lower face height, contributing nothing to the depth increment of the lower face.

Gonion-Menton (Go.M) is the effective height of the mandibular corpus in the pattern representing the resultant effect of the absolute length of the mandibular body, Gonion-Pogonion′ (Go.Po′ a.l.), and its inclination in the pattern, the mandibular plane angle (MPl∡). The greater the mandibular plane angle, the more mandibular corpus size and growth will contribute to the effective height of the lower face and the less to depth (a=c sin A).

Mid-face height measured as Sella-Gonion (S.Go), is the summation of the effective posterior cranial base height, Basion-Sella (Ba.S), and lower posterior face height, Basion-Gonion (Ba.Go), the effective height of the ramus less the superior positioning of Articulare relative to Basion.

The vertical position of the palatal plane and its angular relation to the foramen magnum plane of orientation, Basion Horizontal (BaH), is delineated by Basion-Posterior Nasal Spine (Ba.Pns), Basion-Anterior Nasal Spine (Ba.Ans) and the palatal plane angle to BaH (Pal∡). Because Pns is not visable on the cephalometric X-ray, a constructed Pns is defined as the point of intersection of the Ptm ordinate and the palatal plane. When Pns or Ans is superior to the BaH plane, the position of the landmark is termed plus (+); when inferior, the landmark is termed minus (−). When Ans is inferior to Pns, the palatal plane is tipped down and termed minus (−). When Ans is superior to Pns, the palatal plane is tipped up and termed plus (+).

In quantitating anterior face height, the total anterior face height (N.M) is the summation of the upper face height, Nasion to Anterior Nasal Spine (N.Ans), the lower face height, Anerior Nasal Spine to Menton (Ans.M). Lower face height (Ans.M) is the resultant summation of the effective upper dental height, Anterior Nasal Spine to the incisal edge of the Upper Incisor (Ans.$\underline{1}$), and the effective lower dental height, Menton to the incisal edge of the Lower Incisor (M.$\overline{1}$), minus (−) the overbite or plus (+) the openbite ($\underline{1}.\overline{1}$).

The analysis of the growth process described suggests some change in basic concepts. From the prior art histologically the nasal surface of the palate has been described as resorptive and the oral surface as appositional. Histologically this was to explain the "descent" of the palate during facial growth. The histology is well proven; however, the interpretation of the process is related to the "SN Registration" concept of growth and is subject to question. The explanation of the spatial behavior of the palate during facial growth can best be understood when one relates the palate to the foramen magnum and the cervical vertebrae. For velopharygeal closure, the soft palate must maintain its functional relationship with the anterior arch of the atlas as growth of the posterior cranial base carries the upper face upward and forward away from the foramen magnum. For the palate to maintain its relative position during this growth process, there would have to be resorption on the nasal surface and apposition on the oral surface. The histology is the same but the explanation is more logical.

Whereas the relative position of the palate in the pattern is genetically determined and primarily influenced by growth of the nasal septum, postnatally, palatal behavior is strongly influenced by environmental forces such as respiration, oral function and habits. As space for vertical facial development is created by the divergence of the cranial base and mandibular vectors, the upper face develops, the palate undergoes modification and the teeth erupt to maintain occlusion. Like the upper face, the height of the lower face, although primarily genetically determined by mandibular size, form and position, can be modified by alterations in musculature, respiration and function, affecting the postural relationship of the mandible and thus its effective contribution to lower face depth and height.

Coordinate Dentition Analysis

Figure 8:
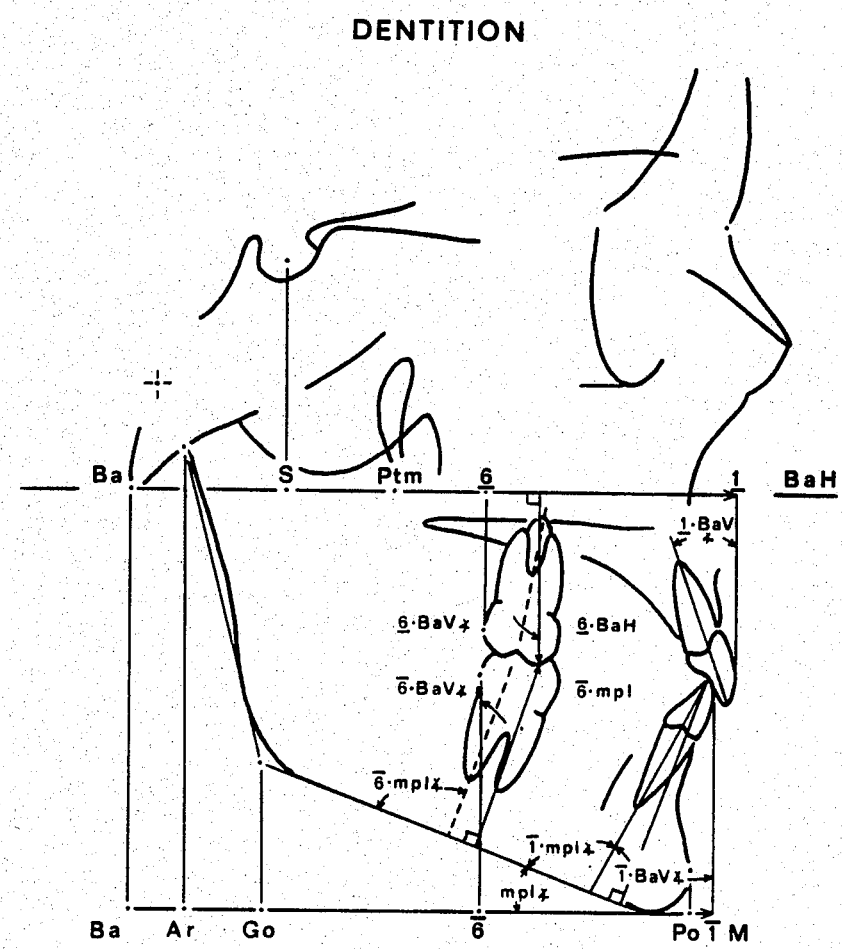
FIG. 8 depicts variants and anatomical landmarks used in the method of the present invention for the dentition.

For purposes of clarity, the dentition analysis is illustrated in FIG. 8. Although presented as a separate illustration, the dentition analysis is not an independent analysis but a continuation of the same quantitation to establish the spatial position of the dentition in the craniofacial pattern. Horizontal or depth spatial positions of the 1st permanent molars and the incisors are measured relative to Basion. Vertical positions of molars and incisors are related to the foramen magnum plane of orientation, Basion Horizontal. Although morphologic skeletal and dental relationships can be readily determined as presented in Table VII, the dentition Analysis was primarily designed for serial usage to quantitate the effects of growth and tooth movement on the spatial positions of the teeth during orthodontic treatment. Table II is the same dentition chart for use in quantitating the change in the spatial positions of the teeth as the result of growth and tooth movement.

(i) Molars

The maxillary 1st permanent molar depth, Basion to the distal of the 1st molar (Ba.$\underline{6}$), is the summation of the effective depth of the posterior cranial base (Ba.S) plus the Sella-Ptm dimension (S.Ptm) plus the upper molar position relative to Ptm (Ptm.$\underline{6}$).

The mandibular 1st permanent molar depth is quantitated in the same manner. Mandibular molar depth, Basion to the distal of the 1st molar (Ba.$\overline{6}$), is the summation of Basion-Articulare (Ba.Ar) plus the effective depth of the ramus inclination (Ar.Go) plus the mandibular molar position in the corpus relative to Gonion (Go.$\overline{6}$). The lower molar is translated forward spatially by growth of the mandible equal to the increase in the total lower face depth (Ba.Po). Therefore, any difference between Ba.Po and Ba.$\overline{6}$ is interpreted as mesial (plus) or distal (minus) movement of the lower molar within the corpus itself and is equal to the change in the $\overline{6}$.Po effective depth. This holds true during most of the growth span with the possible exception of the late stages of facial maturation when apposition and remodeling on the symphysis may be observed.

Vertically, the position of the upper 1st permanent molar is related to Basion Horizontal by measuring the BaV ordinate from Basion Horizontal to the tip of the mesio-buccal cusp of the upper molar ($\underline{6}$.BaH). The inclination of the upper molar is delineated by the angular relation of the long axis of the molar to the BaV ordinate ($\underline{6}$.BaV∡).

Lower 1st permanent molar height is measured as the perpendicular distance from the mandibular plane to the tip of the mesio-buccal cusp of the lower molar ($\overline{6}$.MPl⊥). When the cusp tips are not clearly identified, the cusp tips of both upper and lower molars are taken as a common point of intercuspation. The inclination of the lower molar in the pattern is delineated by the angular relation of the long axis of the lower molar relative to the BaV ordinate ($\overline{6}$.BaV⊥). The inclination of the lower molar in the pattern represents the combined efect of the mandibular plane angle (MPl∡) plus the inclination of the lower molar relative to the mandibular plane ($\overline{6}$.MPl∡). The relationship is expressed by the equation: $\overline{6}.BaV∡ = MPl∡ + \overline{6}MPl∡ - 90°$.

(ii) Incisors

The spatial position of the incisors are similarly recorded relative to Basion. The depth position of the upper incisor relative to Basion is measured from Basion along Basion Horizontal to the labial surface of the upper incisor (Ba.$\underline{1}$). The upper incisor vertical position is measured along the BaV ordinate as the effective height from Basion Horizontal to the incisal edge of the maxillary incisor ($\underline{1}$.BaH). The inclination of the upper incisor in the pattern is measured as the angular relation of its long axis to the BaV ordinate ($\underline{1}$.BaV∡).

The depth position of the lower incisor is measured from Basion to the labial surface of the lower incisor (Ba.$\overline{1}$). Lower incisor height is measured initially as its perpendicular distance form the mandibular plane to the incisal edge of the lower incisor ($\overline{1}$.MPl⊥), then from Menton along the BaV ordinate to the incisal edge as its effective height ($\overline{1}$.M). The lower incisor inclination in the pattern is measured as its long axis angulation to the BaV ordinate ($\overline{1}$.BaV∡) which represents the combined effect of the mandibular plane angle (MPl∡) plus the inclination of the lower incisor relative to the mandibular plane ($\overline{1}$.MPl∡). The relationship is expressed by the equation: $\overline{1}.BaV∡ = MPl∡ + \overline{1}.MPl∡ - 90°$.

Coordinate Profile Analysis

Figure 9:
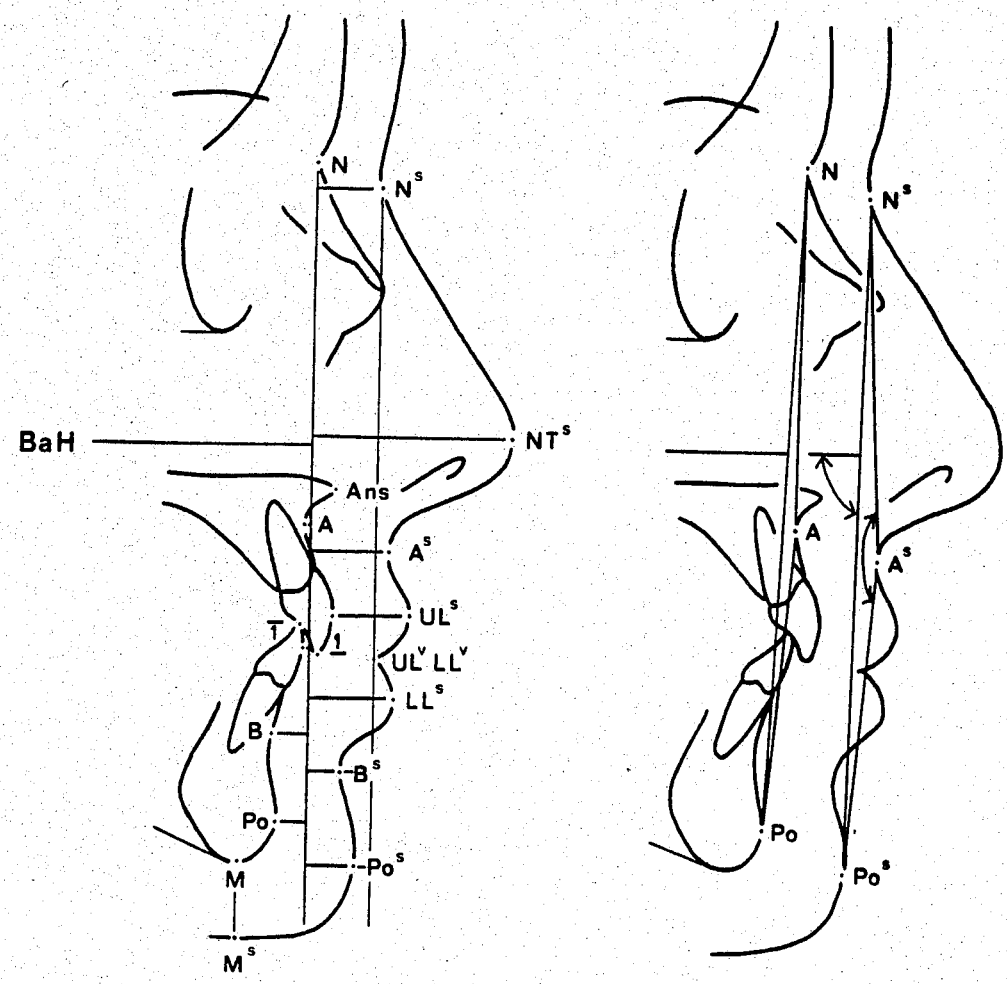
FIG. 9 depicts variants and anatomical landmarks used in the method of the present invention for the profile.

The soft tissue profile analysis (FIG. 9), as a direct extension of the skeletal analysis, makes possible the direct computation of the interrelationship of skeletal growth, soft tissue thickness and resultant soft tissue profile changes. The analysis compares the skeletal and soft tissue profile of the individual and quantitates differences by linear comparison of comparable skeletal and soft tissue landmarks in depth and in height. Coordinate Profile Analysis chart (Example I) is used for serial quantitation of profile changes during growth and orthodontic treatment. The same chart is employed for morphologic cross-sectional studies.

(i) Profile Type

The general facial type of both the skeletal and soft tissue profiles are compared by measurement of the skeletal Facial Angle and Angle of Covexity of Downs, and the comparable soft tissue angles of Downs, as is known in the art.

(ii) Depth

Resultant skeletal profile depth relationships are compared first, recorded as plus (anterior) or minus (posterior) differences relative to the Nasion ordinate (N BaV); i.e., N.Ans, N.A, N.1̲, N.1̅, N.B, N.Po. Second, comparable soft tissue landmarks are recorded as plus or minus differences relative to the Nasion soft tissue ordinate (N$^s$BaV); i.e., N$^s$.Nose tip$^s$, N$^s$.A$^s$, N$^s$.UL$^s$, N$^s$.LL$^s$, N$^s$.B$^s$, N$^s$.Po$^s$. Third, soft tissue thicknesses are recorded as the horizontal difference between comparable hard and soft tissue landmarks; i.e., N.N$^s$, Ans.Nose tip$^s$, A.Nose tip$^s$, A.A$^s$, 1̲.UL$^s$, 1̅.LL$^s$, B.B$^s$, Po.Po$^s$.

(iii) Height

Vertical relations of skeletal profile landmarks are recorded first; i.e., N.M, N.Ans, Ans.1̲, M.1̅, 1̲.1̅, Ans.M. Second, vertical differences of comparable soft tissue profile landmarks are recorded; i.e., N$^s$.M$^s$, N$^s$.Nose tip$^s$, Nose tip$^s$. UL$^v$, M$^s$.LL$^v$, UL$^v$/LL$^v$, Nose tip$^s$.M$^s$. Third, vertical differences between comparable skeletal and soft tissue landmarks are recorded; i.e., N.N$^s$, Ans.Nose tip$^s$, Ans.UL$^v$, 1̲.UL$^v$, 1̅.LL$^v$, M.M$^s$, designated as plus (+) when the soft tissue landmark is superior to the hard tissue landmark and minus (−) when inferior. Fourth, the relationship of profile landmarks relative to the Basion Horizontal plane of orientation are recorded; i.e., BaH.N, BaH.Nose tip$^s$, Ba-H.Ans, BaH.1̲, BaH.UL$^v$, BaH.1̅, BaH.LL$^v$, BaH.M, designated as plus (+) when superior to BaH and minus (−) when inferior to BaH.

Clinical cephalometric analyses may be divided into two general categories. Analyses such as the Downs analysis and the Steiner analysis serve to describe the facial type of an individual and evaluate the parameters of the functional and esthetic balance of the dentition within the particular profile. The second category consists of the craniofacial analyses such as the coordinate analysis, which define the total morphologic pattern and its growth behavior.

Because the coordinate analysis and the Downs analysis employ a common Frankfort horizontal reference plane, the two analyses compliment each other. The Downs analysis appraises the proportionality of the profile by using angular relationships whereas the coordinate analysis explains the Downs analysis in terms of linear measurement and direct proportions of the total craniofacial pattern.

Although morphologic assessment is a major application of the coordinate analysis, its primary contribution lies in its usage as a growth and tooth movement analysis. The same system employed in the morphologic analysis quantitates growth of craniofacial structures and summates their effect on the form of the face, the position of the teeth and the configuration of the profile.

When the coordinate analysis is used as a growth analysis, all serial cephalometric films must be of standard enlargement, all landmarks must be located identically, all graphics must be registered at Basion, and all coordinate graphics must be oriented on the same Basion Horizontal (BaH) axis by maintaining a constant Frankfort horizontal/SN angular relation on all serial illustrations.

When the above serial requirements are followed, the entire Basion Horizontal growth concept may be embodied in a coordinate tracing film, the film serving both as the analyzer, an analog computer and as a graphic illustration of craniofacial growth and tooth movement. The coupling of standardized 8% cephalometric X-ray enlargement and the 8% enlargement registration of the analyzer to correspond with such permits reading and tabulation of measurements in absolute values. With standardized X-ray enlargement and standardized orientation, all that is required to measure and illustrate growth and tooth movement is to superimpose the coordinate grids of serial graphic displays or tracings.

In order to better understand the present invention, the following example is given. This example illustrates the use of a computer in the method of the present invention to quantitate and express cephalometric growth.

EXAMPLE I

Three lateral cephalometric X-rays were taken of John Smith by fixing the X-ray source/head midsagittal plane at a distance of 150 cm with a 120 mm head midsagittal plane/X-ray film position, at ages 8, 13, and 18, to produce X-rays having an 8% enlargement. An Apple plus II with two Apple Disk II drives, Houston Hi-Pad digitizer, Prism IDS printer, and CRT was programmed to compute the variants depicted in FIGS. 5 through 9 from anatomic landmarks shown therein. The three lateral X-rays were serially oriented on the digitizer at basion, with the horizontal coordinates thereof parallel to the X-ray F.H plane of the X-rays, and all of the anatomical coordinates registered in the computer using the digitizer. All variants were computed or summated and stored on disk. The variants of the cranial base, facial depth, and facial height were stored as craniofacial analysis, Table I. The variants of the molars and incisors were stored as dentition analysis, Table II. The variants of profile, depth, and height were stored as profile analysis, Table III. The computer was also programmed to compute variants of the Downs Analyses as set forth on Table IV and the variants of the Steiner Analyses as is known in the art and as set forth in Table V. The computer was selected to run compare and ages 8, 13, and 18 were selected for John Smith. The full craniofacial, dentition and profile analyses were selected for printout comparison whereby Tables I, II, and III were printed. The Downs and Steiner analyses were then selected and Tables IV and V were printed.

The analyses out mode of the computer was then selected for John Smith for age 8. All analyses including craniofacial, dentition, profile, Steiner, and Downs were selected for printout and Tables VI, VII, VIII, IX, and X were produced.

TABLE I

| BASION HORIZONTAL COBEN COORDINATE CRANIOFACIAL ANALYSIS ||||||
| SMITH, JOHN NO: 12345 MALE CA: 08-00 SA: 08-00 09/01/82 BD: 09/01/64 | ORTHO PRE TREATMENT AGE 08-00 | RETENTION AGE 13-00 | POST RETENTION AGE 18-00 | TOTAL |
| --- | --- | --- | --- | --- |
| CRANIAL BASE | | | | |
| BA . S (A. L.) | 38.5 MM | 2.5 MM | 3.0 MM | 5.5 MM |
| BA . S <(S. BA. BAH) | 56.5 DEG | 1.0 DEG | 0.5 DEG | 1.5 DEG |
| BA . S | 21.5 MM | 0.5 MM | 1.5 MM | 2.0 MM |

TABLE I-continued

BASION HORIZONTAL
COBEN COORDINATE CRANIOFACIAL ANALYSIS

SMITH, JOHN
NO: 12345  MALE
CA: 08-00  SA: 08-00
09/01/82  BD: 09/01/64

| | ORTHO PRE TREATMENT AGE 08-00 | RETENTION AGE 13-00 | POST RETENTION AGE 18-00 | TOTAL |
|---|---|---|---|---|
| S . N (A. L.) | 61.5 MM | 3.5 MM | 2.0 MM | 5.5 MM |
| S . F (A. L.) | 54.5 MM | 1.5 MM | 2.0 MM | 3.5 MM |
| F . N (A. L.) | 7.0 MM | 2.0 MM | 0.0 MM | 2.0 MM |
| S . N<(N. S. BAH) | 5.5 DEG | 0.5 DEG | −0.5 DEG | 0.0 DEG |
| S . N | 61.5 MM | 3.0 MM | 2.0 MM | 5.0 MM |
| S<(180+S . N<−BA . S<) | 129.5 DEG | −1.0 DEG | −1.0 DEG | −2.0 DEG |
| FACIAL DEPTH | | | | |
| BA . N | 83.0 MM | 3.5 MM | 3.0 MM | 6.5 MM |
| BA . S | 21.5 MM | 0.5 MM | 1.5 MM | 2.0 MM |
| S . PTM | 16.5 MM | 1.0 MM | 0.0 MM | 1.0 MM |
| PTM . A | 43.5 MM | 3.5 MM | 2.5 MM | 6.0 MM |
| BA . A | 81.5 MM | 5.0 MM | 4.0 MM | 9.0 MM |
| BA . AR | 8.5 MM | 0.0 MM | 0.0 MM | 0.0 MM |
| AR . PO | 66.0 MM | 8.0 MM | 5.0 MM | 13.0 MM |
| BA . B(BA . PO−B. PO) | 74.5 MM | 7.0 MM | 4.0 MM | 11.0 MM |
| BA . PO | 74.5 MM | 8.0 MM | 5.0 MM | 13.0 MM |
| AR . GO(A. L.) | 36.0 MM | 4.5 MM | 6.0 MM | 10.5 MM |
| RI< | 7.0 DEG | −1.0 DEG | 1.0 DEG | 0.0 DEG |
| AR . GO | 4.5 MM | −0.5 MM | 1.5 MM | 1.0 MM |
| GO . PO' (A. L.) | 65.0 MM | 7.5 MM | 3.5 MM | 11.0 MM |
| MPL< | 24.5 DEG | −2.5 DEG | −2.0 DEG | −4.5 DEG |
| B . PO' (A. L.) | 4.0 MM | 0.5 MM | 2.0 MM | 2.5 MM |
| B . PO | 0.0 MM | 1.0 MM | 1.0 MM | 2.0 MM |
| GO . PO | 61.5 MM | 8.5 MM | 3.5 MM | 12.0 MM |
| GO<(90+RI<+MPL<) | 122.0 DEG | −4.0 DEG | −1.0 DEG | −5.0 DEG |
| FACIAL HEIGHT | | | | |
| N . M | 93.0 MM | 9.0 MM | 6.5 MM | 15.5 MM |
| BA . S | 32.0 MM | 2.5 MM | 2.5 MM | 5.0 MM |
| S . N | 6.0 MM | 0.5 MM | 0.0 MM | 0.5 MM |
| BA . N | 38.0 MM | 3.0 MM | 2.5 MM | 5.5 MM |
| BA . GO | 29.5 MM | 5.0 MM | 5.5 MM | 10.5 MM |
| AR . GO | 35.5 MM | 5.0 MM | 5.5 MM | 10.5 MM |
| BA . AR (−) | 6.0 MM | 0.0 MM | 0.0 MM | 0.0 MM |
| GO . M | 25.5 MM | 1.0 MM | −1.5 MM | −0.5 MM |
| BA . M | 55.0 MM | 6.0 MM | 4.0 MM | 10.0 MM |
| S . GO(BA . S+BA . GO) | 61.5 MM | 7.5 MM | 8.0 MM | 15.5 MM |
| BA . PNS | * −3.0 MM | * −1.5 MM | * 1.0 MM | * −0.5 MM |
| BA . ANS | * −5.5 MM | * −0.5 MM | * 0.5 MM | * 0.0 MM |
| PAL< | * −3.0 DEG | * 1.0 DEG | * 0.0 DEG | * 1.0 DEG |
| N . ANS | 43.5 MM | 3.5 MM | 2.0 MM | 5.5 MM |
| ANS . U1 | 20.5 MM | 3.5 MM | 2.0 MM | 5.5 MM |
| M . L1 | 31.5 MM | 2.5 MM | 3.0 MM | 5.5 MM |
| U1/L1 | −2.5 MM | −0.5 MM | −0.5 MM | −1.0 MM |
| ANS . M | 49.5 MM | 5.5 MM | 4.5 MM | 10.0 MM |

TABLE II

BASION HORIZONTAL
COBEN COORDINATE DENTITION ANALYSIS

SMITH, JOHN
NO: 12345  MALE
CA: 08-00  SA: 08-00
09/01/82  BD: 09/01/64

| | ORTHO PRE TREATMENT AGE 08-00 | RETENTION AGE 13-00 | POST RETENTION AGE 18-00 | TOTAL |
|---|---|---|---|---|
| MOLARS | | | | |
| BA . S | 21.5 MM | 0.5 MM | 1.5 MM | 2.0 MM |
| S . PTM | 16.5 MM | 1.0 MM | 0.0 MM | 1.0 MM |
| PTM . U6 | 7.0 MM | 6.0 MM | 2.0 MM | 8.0 MM |
| BA . U6 (DEPTH) | 45.0 MM | 7.5 MM | 3.5 MM | 11.0 MM |
| BA . AR | 8.5 MM | 0.0 MM | 0.0 MM | 0.0 M |
| AR . GO | 4.5 MM | −0.5 MM | 1.5 MM | 1.0 MM |
| GO . L6 | 31.0 MM | 8.0 MM | 3.0 MM | 11.0 MM |
| BA . L6 (DEPTH) | 44.0 MM | 7.5 MM | 4.5 MM | 12.0 MM |
| BA . PO | 74.5 MM | 8.0 MM | 5.0 MM | 13.0 MM |
| L6 . PO | 30.5 MM | 0.5 MM | 0.5 MM | 1.0 MM |
| U6 . BAH (HEIGHT) | 19.0 MM | 5.5 MM | 2.5 MM | 8.0 MM |
| U6 . BAV< | * −13.0 DEG | * 3.5 DEG | * 5.0 DEG | * 8.5 DEG |
| L6 . MPL R<(HEIGHT) | 26.5 MM | 1.0 MM | 2.5 MM | 3.5 MM |
| L6 . BAV< | * 19.0 DEG | * −7.5 DEG | * −4.0 DEG | * −11.5 DEG |
| (MPL<+L6 . MPL<−90) | | | | |
| MPL< | 24.5 DEG | −2.5 DEG | −2.0 DEG | −4.5 DEG |
| L6 . MPL< | 84.5 DEG | −5.0 DEG | −2.0 DEG | −7.0 |
| INCISORS | | | | |
| BA . U1 (DEPTH) | 82.5 MM | 7.5 MM | 3.5 MM | 11.0 MM |

TABLE II-continued

BASION HORIZONTAL
COBEN COORDINATE DENTITION ANALYSIS

SMITH, JOHN  
NO: 12345 MALE  
CA: 08-00  SA: 08-00  
09/01/82  BD: 09/01/64

| | ORTHO PRE TREATMENT AGE 08-00 | | RETENTION AGE 13-00 | | POST RETENTION AGE 18-00 | | TOTAL |
|---|---|---|---|---|---|---|---|
| U1 . BAH (HEIGHT) | | 26.5 MM | | 3.5 MM | | 2.0 MM | 5.5 MM |
| U1 . BAV< | * | 19.5 DEG | * | −2.0 DEG | * | −3.0 DEG | * −5.0 DEG |
| BA . L1 (DEPTH) | | 79.0 MM | | 8.0 MM | | 3.0 MM | 11.0 MM |
| L1 . MPL R<(HEIGHT) | | 33.0 MM | | 2.0 MM | | 2.0 MM | 4.0 MM |
| L1 . M (HEIGHT) | | 31.5 MM | | 2.5 MM | | 3.0 MM | 5.5 MM |
| L1 . BAV< | * | 30.0 DEG | * | 1.0 DEG | * | −7.5 DEG | * −6.5 DEG |
| (MPL<+L1 . MPL<−90) | | | | | | | |
| MPL< | | 24.5 DEG | | −2.5 DEG | | −2.0 DEG | −4.5 DEG |
| L1 . MPL< | | 95.5 DEG | | 3.5 DEG | | −5.5 DEG | −2.0 DEG |

TABLE III

BASION HORIZONTAL
COBEN COORDINATE PROFILE ANALYSIS

SMITH, JOHN  
NO: 12345 MALE  
CA: 08-00  SA: 08-00  
09/01/82  BD: 09/01/64

| | ORTHO PRE TREATMENT AGE 08-00 | | RETENTION AGE 13-00 | | POST RETENTION AGE 18-00 | | TOTAL |
|---|---|---|---|---|---|---|---|
| PROFILE | | | | | | | |
| SKELETAL PROFILE | | | | | | | |
| FACIAL< | | 84.5 DEG | | 87.5 DEG | | 89.0 DEG | 4.5 DEG |
| CONVEXITY< | * | 8.0 DEG | * | 5.5 DEG | * | 3.5 DEG | * −4.5 DEG |
| SOFT TISSUE PROFILE | | | | | | | |
| FACIAL< | | 87.5 DEG | | 88.0 DEG | | 88.0 DEG | 0.5 DEG |
| CONVEXITY< | * | 18.0 DEG | * | 18.5 DEG | * | 16.5 DEG | * −1.5 DEG |
| DEPTH | | | | | | | |
| SKELETAL PROFILE | | | | | | | |
| N . ANS | * | 2.0 MM | * | 4.0 MM | * | 5.0 MM | * 3.0 MM |
| N . A | * | −1.5 MM | * | 0.5 MM | * | 5.0 MM | * 3.0 MM |
| N . U1 | * | −0.5 MM | * | 3.5 MM | * | 4.0 MM | * 4.5 MM |
| N . L1 | * | −4.0 MM | * | 0.5 MM | * | 0.0 MM | * 4.0 MM |
| N . B | * | −8.5 MM | * | −4.5 MM | * | −3.5 MM | * 5.0 MM |
| N . PO | * | −8.5 MM | * | −4.0 MM | * | −2.0 MM | * 6.5 MM |
| SOFT TISSUE PROFILE | | | | | | | |
| $N_5$ . NOSE TIP$^5$ | * | 17.0 MM | * | 22.5 MM | * | 25.5 MM | * 8.5 MM |
| $N^5$ . $A^5$ | * | 4.5 MM | * | 9.0 MM | * | 9.0 MM | * 4.5 MM |
| $N^5$ . $UL^5$ | * | 6.5 MM | * | 11.5 MM | * | 11.0 MM | * 4.5 MM |
| $N^5$ . $LL^5$ | * | 4.0 MM | * | 9.5 MM | * | 9.0 MM | * 5.0 MM |
| $N^5$ . $B^5$ | * | −2.0 MM | * | 1.5 MM | * | 1.0 MM | * 3.0 MM |
| $N^5$ . $PO^5$ | * | −4.0 MM | * | 3.0 MM | * | 3.0 MM | * 7.0 MM |
| SOFT TISS. THICKNESS | | | | | | | |
| N . $N^5$ | | 4.5 MM | | 5.0 MM | | 6.0 MM | 1.5 MM |
| ANS . NOSE TIP$^5$ | | 19.5 MM | | 23.0 MM | | 26.5 MM | 7.0 MM |
| A . NOSE TIP$^5$ | | 23.5 MM | | 27.0 MM | | 31.0 MM | 7.5 MM |
| A . $A^5$ | | 10.5 MM | | 14.0 MM | | 14.5 MM | 4.0 MM |
| U1 . $UL^5$ | | 11.5 MM | | 13.0 MM | | 13.0 MM | 1.5 MM |
| L1 . $LL^5$ | | 12.5 MM | | 14.0 MM | | 15.0 MM | 2.5 MM |
| B . $B^5$ | | 11.0 MM | | 11.5 MM | | 11.0 MM | 0.0 MM |
| PO . $PO^5$ | | 9.0 MM | | 12.0 MM | | 11.0 MM | 2.0 MM |
| HEIGHT | | | | | | | |
| SKELETAL PROFILE | | | | | | | |
| N . M | | 93.0 MM | | 102.0 MM | | 108.5 MM | 15.5 MM |
| N . ANS | | 43.5 MM | | 47.0 MM | | 49.0 MM | 5.5 MM |
| ANS . U1 | | 20.5 MM | | 24.0 MM | | 26.0 MM | 5.5 MM |
| M . L1 | | 31.5 MM | | 34.0 MM | | 37.0 MM | 5.5 MM |
| U1 . L1 | | −2.5 MM | | −3.0 MM | | −3.5 MM | −1.0 MM |
| ANS . M | | 49.5 MM | | 55.0 MM | | 59.5 MM | 10.0 MM |
| SOFT TISSUE PROFILE | | | | | | | |
| $N^5$ . $M^5$ | | 101.0 MM | | 112.5 MM | | 118.0 MM | 17.0 MM |
| $N^5$ . NOSE TIP$^5$ | | 30.5 MM | | 35.0 MM | | 38.0 MM | 7.5 MM |
| NOSE TIP$^5$ . $UL^V$ | | 28.5 MM | | 30.0 MM | | 32.5 MM | 4.0 MM |
| $M^5$ . $LL^V$ | | 42.0 MM | | 47.5 MM | | 47.5 MM | 5.5 MM |
| $UL^V$ . $LL^V$ | | 0.0 MM | | 0.0 MM | | 0.0 MM | 0.0 MM |
| NOSE TIP$^5$ . $M^5$ | | 70.5 MM | | 77.5 MM | | 80.0 MM | 9.5 MM |
| SKELETAL-SOFT TISSUE | | | | | | | |
| N . $N^5$ | * | −5.0 MM | * | −3.0 MM | * | −2.0 MM | * 3.0 MM |
| ANS . NOSE TIP$^5$ | * | 8.5 MM | * | 9.5 MM | * | 9.0 MM | * 0.5 MM |
| ANS . $UL^V$ | * | −19.5 MM | * | −21.0 MM | * | −23.5 MM | * −4.0 MM |
| U1 . $UL^V$ | * | 1.0 MM | * | 3.0 MM | * | 3.0 MM | * 2.0 MM |
| L1 . $LL^V$ | * | −1.5 MM | * | 0.0 MM | * | −0.5 MM | * 1.0 MM |
| M . $M^5$ | * | −12.0 MM | * | −13.5 MM | * | −11.5 MM | * 0.5 MM |
| BAH RELATIONSHIP | | | | | | | |
| BAH . N | * | 38.5 MM | * | 41.5 MM | * | 43.5 MM | * 5.0 MM |

TABLE III-continued
BASION HORIZONTAL
COBEN COORDINATE PROFILE ANALYSIS

SMITH, JOHN  
NO: 12345 MALE  
CA: 08-00 SA: 08-00  
09/01/82 BD: 09/01/64

| | ORTHO PRE TREATMENT AGE 08-00 | | RETENTION AGE 13-00 | | POST RETENTION AGE 18-00 | | TOTAL |
|---|---|---|---|---|---|---|---|
| BAH . NOSE TIP[5] | * | 3.0 MM | * | 3.5 MM | * | 3.5 MM | * | 0.5 MM |
| BAH . ANS | * | −5.5 MM | * | −6.0 MM | * | −5.5 MM | * | 0.0 MM |
| BAH . U1 | * | −26.5 MM | * | −30.0 MM | * | −32.0 MM | * | −5.5 MM |
| BAH . UL[V] | * | −25.5 MM | * | −27.0 MM | * | 29.0 MM | * | −3.5 MM |
| BAH . L1 | * | −23.5 MM | * | −27.0 MM | * | −28.5 MM | * | −5.0 MM |
| BAH . LL[V] | * | −25.0 MM | * | −27.0 MM | * | −25.0 MM | * | −4.0 MM |
| BAH . M | * | −55.5 MM | * | −61.0 MM | * | −65.5 MM | * | −10.0 MM |

TABLE IV
DOWNS ANALYSIS

SMITH, JOHN  
NO: 12345 MALE  
CA: 08-0010 SA: 08-00  
09/01/82 BD: 09/01/64

| | ORTHO PRE TREATMENT AGE 08-00 | | RETENTION AGE 13-00 | | POST RETENTION AGE 18-00 | | TOTAL |
|---|---|---|---|---|---|---|---|
| SKELETAL | | | | | | | | |
| FACIAL ANGLE | | 84.5 DEG | | 87.5 DEG | | 89.0 DEG | | 4.5 DEG |
| ANGLE CONVEXITY | * | 8.0 DEG | * | 5.5 DEG | * | 3.5 DEG | * | −4.5 DEG |
| A/B FACIAL PL | * | −6.5 DEG | * | −6.0 DEG | * | −6.0 DEG | * | 0.5 DEG |
| MAND PL ANGLE | | 24.5 DEG | | 22.0 DEG | | 20.0 DEG | | −4.5 DEG |
| Y AXIS | | 60.0 DEG | | 58.5 DEG | | 58.5 DEG | | −1.5 DEG |
| DENTITION | | | | | | | | |
| OCCLUSAL PL | * | −12.5 DEG | * | −8.5 DEG | * | −7.0 DEG | * | 5.5 DEG |
| L1/OCCLUSAL PL | * | 18.0 DEG | * | 22.0 DEG | * | 16.5 DEG | * | −1.5 DEG |
| L1/MAND PL | * | 5.5 DEG | * | 8.5 DEG | * | 3.0 DEG | * | −2.5 DEG |
| U1/L1 ANGLE | | 130.5 DEG | | 132.0 DEG | | 142.5 DEG | | 12.0 DEG |
| U1/APO ANGLE | * | 29.0 DEG | * | 22.5 DEG | * | 17.0 DEG | * | −12.0 DEG |
| U1/APO | * | 2.5 MM | * | 3.5 MM | * | 2.5 MM | * | 0.0 MM |
| L1/APO ANGLE | * | 20.5 DEG | * | 25.5 DEG | * | 20.5 DEG | * | 0.0 DEG |
| L1/APO | * | 0.0 MM | * | 1.0 MM | * | 0.0 MM | * | 0.0 MM |

TABLE 5
STEINER ANALYSIS

SMITH, JOHN  
NO: 12345 MALE  
CA: 08-0010 SA: 08-00  
09/01/82 BD: 09/01/64

| | ORTHO PRE TREATMENT AGE 08-00 | | RETENTION AGE 13-00 | | POST RETENTION AGE 18-00 | | TOTAL |
|---|---|---|---|---|---|---|---|
| SNA ANGLE | | 82.5 DEG | | 84.5 DEG | | 85.0 DEG | | 2.5 DEG |
| SNB ANGLE | | 78.5 DEG | | 81.0 DEG | | 82.0 DEG | | 3.5 DEG |
| ANB ANGLE | | 4.5 DEG | | 3.5 DEG | | 3.0 DEG | | −1.5 DEG |
| U1/NA ANGLE | * | 21.0 DEG | * | 17.0 DEG | * | 13.5 DEG | * | −7.5 DEG |
| U1/NA | * | 0.0 MM | * | 1.5 MM | * | 1.5 MM | * | 1.5 MM |
| L1/NB ANGLE | * | 130.5 DEG | * | 132.0 DEG | * | 142.5 DEG | * | 12.0 DEG |
| L1/NB | * | 24.0 MM | * | 27.5 MM | * | 21.0 MM | * | −3.0 MM |
| U1/L1 ANGLE | | 2.5 DEG | | 3.5 DEG | | 2.5 DEG | | 0.0 DEG |

TABLE VI
BASION HORIZONTAL
COBEN COORDINATE CRANIOFACIAL ANALYSIS

SMITH, JOHN  
NO: 12345 MALE  
CLASS: I  
CA: 08-00 SA: 08-00  
09/01/82 BD: 09/01/64

AGE 8 YRS. +/− 1 YR. MALE-FEMALE (08-00)

| | LINEAR | MEAN | S. D. | PROPORTIONS | MEAN | S. D. |
|---|---|---|---|---|---|---|
| CRANIAL BASE | | | | | | |
| BA . S (A. L.) | 38.5 MM | 38.9 | 2.25 | | | |
| BA . S<(S. BA. BAH) | 56.5 DEG | 57.5 | 3.61 | | | |
| BA . S | 21.5 MM | 20.7 | 2.42 | | | |
| S . N (A. L.) | 61.5 MM | 63.0 | 2.44 | | | |
| S . F (A. L.) | 54.5 MM | 57.8 | 2.54 | | | |
| F . N (A. L.) | 7.0 MM | 5.2 | 1.74 | | | |
| S . N<(N. S. BAH) | 5.5 DEG | 6.3 | 3.19 | | | |
| S . N | 61.5 MM | 62.4 | 2.51 | | | |
| S<(180+S . N<−BA . S<) | 129.5 DEG | 128.8 | 4.56 | | | |
| FACIAL DEPTH | | | | | | |
| BA . N | 83.0 MM | 83.1 | 3.75 | | | |
| BA . S | 21.5 MM | 20.7 | 2.42 | 25.9% BA . N | 24.9 | 2.16 |

TABLE VI-continued
BASION HORIZONTAL
COBEN COORDINATE CRANIOFACIAL ANALYSIS SMITH, JOHN  
NO: 12345   MALE  
CLASS: I  
CA: 08-00   SA: 08-00  
09/01/82   BD: 09/01/64

AGE 8 YRS. +/− 1 YR. MALE-FEMALE (08-00)

|  | LINEAR |  | MEAN | S. D. | PROPORTIONS | MEAN | S. D. |
|---|---|---|---|---|---|---|---|
| S . PTM | 16.5 | MM | 17.2 | 1.90 | 19.9% BA . N | 20.7 | 2.47 |
| PTM . A | 43.5 | MM | 42.7 | 1.96 | 52.4% BA . N | 51.4 | 2.59 |
| BA . A | 81.5 | MM | 80.6 | 3.50 | 98.2% BA . N | 97.0 | 3.24 |
| BA . AR | 8.5 | MM | 8.3 | 2.31 | 10.2% BA . N | 9.9 | 2.60 |
| AR . PO | 66.0 | MM | 66.7 | 4.86 | 79.5% BA . N | 80.2 | 6.48 |
| BA . B(BA . PO-B. PO) | 74.5 | MM | 74.9 | 4.49 | 89.8% BA . N | 90.1 | 5.50 |
| BA . PO | 74.5 | MM | 74.9 | 5.23 | 89.8% BA . N | 90.1 | 6.38 |
| AR . GO (A. L.) | 36.0 | MM | 37.6 | 2.97 | 43.4% BA . N | 45.2 | 3.20 |
| RI< | 7.0 | DEG | 9.8 | 4.98 |  |  |  |
| AR . GO | 4.5 | MM | 6.3 | 3.26 | 5.4% BA . N | 7.6 | 3.95 |
| GO . PO' (A. L.) | 65.0 | MM | 64.1 | 2.87 | 78.3% BA . N | 76.9 | 3.99 |
| MPL< | 24.5 | DEG | 26.4 | 4.07 |  |  |  |
| B . PO' (A. L.) | 4.0 | MM | 5.1 | 1.76 | 4.8% BA . N | 6.1 | 2.09 |
| B . PO | 0.0 | MM | 0.0 | 1.47 | 0.0% BA . N | 0.0 | 1.78 |
| GO . PO | 61.5 | MM | 60.3 | 3.50 | 74.1% BA . N | 72.6 | 4.44 |
| GO<(90+RI<+MPL<) | 122.0 | DEG | 126.2 | 5.41 |  |  |  |
| FACIAL HEIGHT |  |  |  |  |  |  |  |
| N . M | 92.0 | MM | 95.7 | 4.46 | 112.0% BA . N | 115.3 | 6.56 |
| BA . S | 32.0 | MM | 32.6 | 2.26 | 34.4% N . M | 34.1 | 2.28 |
| S . N | 6.0 | MM | 6.8 | 3.49 | 6.5% N . M | 7.1 | 3.68 |
| BA . N | 38.0 | MM | 39.4 | 3.86 | 40.9% N . M | 41.2 | 3.80 |
| BA . GO | 29.5 | MM | 29.6 | 3.52 | 31.7% N . M | 30.9 | 3.27 |
| AR . GO | 35.5 | MM | 36.9 | 2.94 | 38.2% N . M | 38.5 | 2.76 |
| BA . AR (−) | 6.0 | MM | −7.3 | 1.80 | 6.5% N . M | −7.6 | 1.96 |
| GO . M | 25.5 | MM | 26.7 | 3.56 | 27.4% N . M | 27.9 | 3.35 |
| BA . M | 55.0 | MM | 56.3 | 4.80 | 59.1% N . M | 58.8 | 3.81 |
| S . GO(BA . S+BA . GO) | 61.5 | MM | 62.3 | 4.19 | 66.1% N . M | 65.0 | 3.79 |
| BA . PNS | * −3.0 | MM | −2.1 | 2.84 | −3.2% N . M | −2.2 | 2.83 |
| BA . ANS | * −5.5 | MM | −4.4 | 4.52 | −5.9% N . M | −4.6 | 4.68 |
| PAL< | * −3.0 | DEG | −2.7 | 3.88 |  |  |  |
| N . ANS | 43.5 | MM | 43.8 | 2.73 | 46.8% N . M | 45.8 | 2.18 |
| ANS . U1 | 20.5 | MM | 22.8 | 2.27 | 22.0% N . M | 23.8 | 2.18 |
| M . L1 | 31.5 | MM | 32.1 | 2.28 | 33.9% N . M | 33.4 | 1.76 |
| U1/L1 | −2.5 | MM | −3.0 | 2.37 | −2.7% N . M | −3.0 | 2.45 |
| ANS . M | 49.5 | MM | 51.9 | 3.22 | 53.2% N . M | 54.2 | 2.18 |

TABLE VII
BASION HORIZONTAL
COBEN COORDINATE DENTITION ANALYSIS

SMITH, JOHN  
NO: 12345   MALE  
CLASS: I  
CA: 08-00   SA: 08-00  
09/01/82   BD: 09/01/64

AGE 8 YRS. +/− 1 YR. MALE-FEMALE (08-00)

|  | LINEAR |  | MEAN | S. D. | PROPORTIONS | MEAN | S. D. |
|---|---|---|---|---|---|---|---|
| MOLARS |  |  |  |  |  |  |  |
| BA . S | 21.5 | MM | 20.7 | 2.42 | 25.9% BA . N | 24.9 | 2.16 |
| S . PTM | 16.5 | MM | 17.2 | 1.90 | 19.9% BA . N | 24.9 | 2.16 |
| PTM . U6 | 7.0 | MM | 2.2 | 2.22 | 8.4% BA . N | 7.5 | 2.58 |
| BA . U6 (DEPTH) | 45.0 | MM | 44.1 | 3.75 | 54.2% BA . N | 53.1 | 3.56 |
| BA . AR | 8.5 | MM | 8.3 | 2.31 | 10.2% BA . N | 9.9 | 2.60 |
| AR . GO | 4.5 | MM | 6.3 | 3.26 | 5.4% BA . N | 7.6 | 3.95 |
| GO . L6 | 31.0 | MM | 29.3 | 3.07 | 37.3% BA . N | 35.2 | 3.15 |
| BA . L6 (DEPTH) | 44.0 | MM | 43.9 | 3.76 | 53.0% BA . N | 52.7 | 3.83 |
| BA . PO | 74.5 | MM | 74.9 | 5.23 | 84.8% BA . N | 90.1 | 6.38 |
| L6 . PO | 30.5 | MM | 31.0 | 2.96 | 36.7% BA . N | 37.4 | 4.16 |
| U6 . BAH (HEIGHT) | 19.0 | MM | 19.6 | 4.50 | 20.4% N . M | 20.4 | 4.58 |
| U6 . BAV< | * −13.0 | DEG | −16.0 | 5.72 |  |  |  |
| L6 . MPL R<(HEIGHT) | 26.5 | MM | 26.3 | 1.64 | 28.5% N . M | 27.5 | 1.31 |
| L6 . BAV< | * 19.0 | DEG | +22.1 | 6.07 |  |  |  |
| (MPL<+L6 . MPL<−90) |  |  |  |  |  |  |  |
| MPL< | 24.5 | DEG | 26.4 | 4.07 |  |  |  |
| L6 . MPL< | 84.5 | DEG | 85.7 | 4.77 |  |  |  |
| INCISORS |  |  |  |  |  |  |  |
| BA . U1 (DEPTH) | 82.5 | MM | 83.7 | 4.54 | 99.4% BA . N | 100.7 | 4.09 |
| U1 . BAH (HEIGHT) | 26.5 | MM | 27.0 | 5.17 | 28.5% N . M | 28.2 | 5.10 |
| U1 . BAV< | * 19.5 | DEG | +17.9 | 8.67 |  |  |  |
| BA . L1 (DEPTH) | 79.0 | MM | 80.2 | 4.66 | 95.2% BA . N | 96.6 | 4.88 |
| L1 . MPL R<(HEIGHT) | 33.0 | MM | 33.7 | 2.33 | 35.5% N . M | 35.2 | 1.82 |
| L1 . M (HEIGHT) | 31.5 | MM | 32.1 | 2.28 | 33.9% N . M | 33.4 | 1.76 |
| L1 . BAV< | * 30.0 | DEG | +28.6 | 6.60 |  |  |  |
| (MPL<+L1 . MPL<−90) |  |  |  |  |  |  |  |

TABLE VII-continued

BASION HORIZONTAL
COBEN COORDINATE DENTITION ANALYSIS

SMITH, JOHN
NO: 12345 MALE
CLASS: I
CA: 08-00 SA: 08-00
09/01/82 BD: 09/01/64

AGE 8 YRS. +/− 1 YR. MALE-FEMALE (08-00)

| | LINEAR | MEAN | S. D. | PROPORTIONS | MEAN | S. D. |
|---|---|---|---|---|---|---|
| MPL< | 24.5 DEG | 26.4 | 4.07 | | | |
| L1 . MPL< | 95.5 DEG | 92.2 | 6.66 | | | |

TABLE VIII

BASION HORIZONTAL
COBEN COORDINATE PROFILE ANALYSIS

SMITH, JOHN
NO: 12345 MALE
CLASS: I
CA: 08-00 SA: 08-00
09/01/82 BD: 09/01/64

AGE 8 YRS. +/− 1 YR. MALE-FEMALE (08-00)

| | | LINEAR | MEAN | S. D. | PROPORTIONS | MEAN | S. D. |
|---|---|---|---|---|---|---|---|
| PROFILE | | | | | | | |
| SKELETAL PROFILE | | | | | | | |
| FACIAL< | | 84.5 DEG | | | | | |
| CONVEXITY< | * | 8.0 DEG | | | | | |
| SOFT TISSUE PROFILE | | | | | | | |
| FACIAL< | | 87.5 DEG | | | | | |
| CONVEXITY< | * | 18.0 DEG | | | | | |
| DEPTH | | | | | | | |
| SKELETAL PROFILE | | | | | | | |
| N . ANS | * | 2.0 MM | | | | | |
| N . A | * | −1.5 MM | | | | | |
| N . U1 | * | −0.5 MM | | | | | |
| N . L1 | * | −4.0 MM | | | | | |
| N . B | * | −8.5 MM | | | | | |
| N . PO | * | −8.5 MM | | | | | |
| SOFT TISSUE PROFILE | | | | | | | |
| $N_5$ . NOSE TIP$^5$ | * | 17.0 MM | | | | | |
| $N^5$ . $A^5$ | * | 4.5 MM | | | | | |
| $N^5$ . $UL^5$ | * | 6.5 MM | | | | | |
| $N^5$ . $LL^5$ | * | 4.0 MM | | | | | |
| $N^5$ . $B^5$ | * | −2.0 MM | | | | | |
| $N^5$ . $PO^5$ | * | −4.0 MM | | | | | |
| SOFT TISS. THICKNESS | | | | | | | |
| N . $N^5$ | | 4.5 MM | | | | | |
| ANS . NOSE TIP$^5$ | | 19.5 MM | | | | | |
| A . NOSE TIP$^5$ | | 23.5 MM | | | | | |
| A . $A^5$ | | 10.5 MM | | | | | |
| U1 . $UL^5$ | | 11.5 MM | | | | | |
| L1 . $LL^5$ | | 12.5 MM | | | | | |
| B . $B^5$ | | 11.0 MM | | | | | |
| PO . $PO^5$ | | 9.0 MM | | | | | |
| HEIGHT | | | | | | | |
| SKELETAL PROFILE | | | | | | | |
| N . M | | 93.0 MM | | | | | |
| N . ANS | | 43.5 MM | | | | | |
| ANS . U1 | | 20.5 MM | | | | | |
| M . L1 | | 31.5 MM | | | | | |
| U1 . L1 | | −2.5 MM | | | | | |
| ANS . M | | 49.5 MM | | | | | |
| SOFT TISSUE PROFILE | | | | | | | |
| $N^5$ . $M^5$ | | 101.0 MM | | | | | |
| $N^5$ . NOSE TIP$^5$ | | 30.5 MM | | | | | |
| NOSE TIP$^5$ . $UL^V$ | | 28.5 MM | | | | | |
| $M^5$ . $LL^V$ | | 42.0 MM | | | | | |
| $UL^V$ . $LL^V$ | | 0.0 MM | | | | | |
| NOSE TIP$^5$ . $M^5$ | | 70.5 MM | | | | | |
| SKELETAL-SOFT TISSUE | | | | | | | |
| N . $N^5$ | * | −5.0 MM | | | | | |
| ANS . NOSE TIP$^5$ | * | 8.5 MM | | | | | |
| ANS . $UL^V$ | * | −19.5 MM | | | | | |
| U1 . $UL^V$ | * | 1.0 MM | | | | | |
| L1 . $LL^V$ | * | −1.5 MM | | | | | |
| M . $M^5$ | * | −12.0 MM | | | | | |
| BAH RELATIONSHIP | | | | | | | |
| BAH . N | * | 38.5 MM | | | | | |
| BAH . NOSE TIP$^5$ | * | 3.0 MM | | | | | |
| BAH . ANS | * | −5.5 MM | | | | | |
| BAH . U1 | * | −26.5 MM | | | | | |

TABLE VIII-continued

BASION HORIZONTAL
COBEN COORDINATE PROFILE ANALYSIS

SMITH, JOHN
NO: 12345  MALE
CLASS: I
CA: 08-00  SA: 08-00
09/01/82  BD: 09/01/64

AGE 8 YRS. +/− 1 YR. MALE-FEMALE   (08-00)

| | | LINEAR | MEAN | S. D. | PROPORTIONS | MEAN | S. D. |
|---|---|---|---|---|---|---|---|
| BAH . UL$^V$ | * | −25.5 MM | | | | | |
| BAH . L1 | * | −23.5 MM | | | | | |
| BAH . LL$^V$ | * | −25.0 MM | | | | | |
| BAH . M | * | −55.5 MM | | | | | |

TABLE IX

DOWNS ANALYSIS

SMITH, JOHN
NO: 12345  MALE
CLASS: I
CA: 08-00  SA: 08-00
09/01/82  BD: 09/01/64

AGE 12 YRS.-17YRS.   (08-00)
WHITE MALE-FEMALE

| | | LINEAR | MEAN | S. D. | MIN | MAX |
|---|---|---|---|---|---|---|
| SKELETAL | | | | | | |
| FACIAL ANGLE | | 84.5 DEG | 87.8 | 3.57 | 82.0 | 95.0 |
| ANGLE CONVEXITY | * | 8.0 DEG | 0.0 | 5.09 | −8.5 | +10.0 |
| A/B FACIAL PL | * | −6.5 DEG | −4.6 | 3.67 | −9.0 | 0.0 |
| MAND PL ANGLE | | 24.5 DEG | 21.9 | 3.24 | 17.0 | 28.0 |
| Y AXIS | | 60.0 DEG | 59.4 | 3.82 | 53.0 | 66.0 |
| DENTITION | | | | | | |
| OCCLUSAL PL | * | −12.5 DEG | −9.3 | 3.83 | −1.5 | −14.0 |
| L1/OCCLUSAL PL | * | 18.0 DEG | +14.5 | 3.48 | +3.5 | +20.0 |
| L1/MAND PL | * | 5.5 DEG | +1.4 | 3.78 | −8.5 | +7.0 |
| U1/L1 ANGLE | | 130.5 DEG | 135.4 | 5.76 | 130.0 | 150.5 |
| U1/APO ANGLE | * | 29.0 DEG | 21.6 | | | |
| U1/APO | * | 2.5 MM | 2.7 | 1.80 | −1.0 | +5.0 |
| L1/APO ANGLE | * | 20.5 DEG | 23.0 | | | |
| L1/APO | * | 0.0 MM | 0.0 | | −2.0 | +3.0 |

TABLE X

STEINER ANALYSIS

SMITH, JOHN
NO: 12345  MALE
CLASS: I
CA: 08-00  SA: 08-00
09/01/82  BD: 09/01/64

AGE NOT SPECIFIED   (08-00)
WHITE MALE-FEMALE

| | | LINEAR | MEAN | S. D. | MIN | MAX |
|---|---|---|---|---|---|---|
| SNA ANGLE | | 82.5 DEG | 82.0 | | | |
| SNB ANGLE | | 78.5 DEG | 80.0 | | | |
| ANB ANGLE | | 4.5 DEG | 2.0 | | | |
| U1/NA ANGLE | * | 21.0 DEG | 22.0 | | | |
| U1/NA | * | 0.0 MM | 4.0 | | | |
| L1/NB ANGLE | * | 130.5 DEG | 25.0 | | | |
| L1/NB | * | 24.0 MM | 4.0 | | | |
| U1/L1 ANGLE | | 2.5 DEG | 131.0 | | | |

While the foregoing example exemplifies operational modes for use of a computer with the present invention, it should be understood that any subset of variants may be selected for analyses, comparison, and the like. Additionally, Tables VI through X further illustrate that a data base for given ages including, for example, mean and standard deviation values for all variants are created and stored in the computer (disks). Moreover, the computer may be programmed to replicate graphic illustrations for the various analyses or subsets of their variants, including replication of serial tracings such as are depicted in FIG. 4.

A morphologic analysis as in Tables VI through VIII is used to describe the size and proportionality of a facial pattern to determine the extent to which such variants affect the relationship of the dentition. A therapeutic program is designed to either harmoniously conform the teeth to the particular facial pattern or to utilize the growth potential of the face in the correction of a malocclusion to achieve such harmonious relationship in the mature face.

The growth measurement analyses as in Tables I through III allows the clinician to monitor the growth and tooth movement in a face at any time during treatment, thereby permitting the clinician to modify the treatment procedure to conform with the potential of the individual face. The method also permits one to analyze the total behavior at the end of treatment (retention) and the post-treatment behavior of the face and dentition as it develops to maturity.

The same method is utilized by the maxillo-facial surgeon to measure areas of disharmony of the face. A surgical blueprint is formulated to correct the disharmony by repositioning certain landmarks. The repositioned landmarks are in-putted to determine surgical repositioning of dento-facial structures.

What is claimed is:

1. A method for the cephalometric quantitation and expression of growth of a patient comprising the steps of:
   (a) taking a lateral cephalometric X-ray of a patient having a predetermined enlargement factor by fixing the X-ray source/head midsagittal plane distance;
   (b) registering an analyzer with said X-ray such that said analyzer is registered at the anatomic landmark basion and oriented with the horizontal components of said analyzer paralleling the X-ray Frankfort Horizontal plane of said X-ray;
   (c) registering anatomic landmarks of cephalometric regions having contributing variants sought to be quantified with said analyzer, said regions selected from the group consisting of cranial base, facial depth, facial height, dentition, and profile, wherein said registering step includes generating the linear size, proportions and angular relationships of said variants;
   (d) summating the linear size, proportions and angular relationships of said variants for the cephalometric regions using said analyzer; and
   (e) retaining the results of said summating step for future reference in treatment of said patient.

2. The method of claim 1, wherein said analyzer comprises a computer having a digitizer, said digitizer being oriented in the same manner as said analyzer and to read said X-ray at said predetermined enlargement factor, said digitizer reading said anatomic landmarks and determining coordinates which are registered in said computer, said computer summating and recording said variants.

3. The method of claim 2, wherein said computer further includes a CRT, said computer further programmed to replicate graphics depicting said X-ray image of said cephalometric regions together with said variants, on said CRT.

4. The method of claim 3, wherein said computer is programmed to print out in tabular form for each said region, said variants.

5. The method of claim 4, wherein said computer is programmed to print out said graphics.

6. The method of claim 1, further including the step of comparing said recorded results with tabulated values for the mean and standard deviation of said variants in formulating a treatment for said patient of determined age.

7. The method of claim 6, further including the steps of identifying areas of disharmony, making a plan for correction of said areas of disharmony, said plan creating new landmark locations, registering said new landmark locations with said analyzer, and performing said summating step.

8. The method of claim 1, further including the steps of summating said variants relating to depth including said facial depth, and said dentition, as a percentage of Ba.N, and summating said variants relating to height including said facial height and said dentition, as a percentage of N.M, whereby the proportions relating to cranial base depth and cranial base height are determined.

9. The method of claim 1 wherein steps (a) through (e) are repeated at least once at a time later than when said steps were originally performed and said variants are compared for purposes of determining areas of growth and tooth movement.

10. A method for the cephalometric quantitation and expression of growth of a patient with the aid of a computer comprising the steps of:
   (a) taking a lateral cephalometric X-ray of a patient having a predetermined enlargement factor by fixing the X-ray source/midsagittal plane distance;
   (b) registering anatomic coordinates of cephalometric regions selected from the group consisting of cranial base, facial depth, facial height, dentition, and profile, said regions comprising contributing variants sought to be quantified, said registering accomplished by having said computer identify anatomic landmarks and compute said coordinates from said X-ray in a manner wherein said computer is registered at said anatomic landmark basion and oriented to align its horizontal components to parallel the Frankfort horizontal plane of said X-ray;
   (c) summating the linear size, proportion and angular relationships of said variants for the cephalometric regions; wherein said variants for said cranial base are selected from the group consisting of Ba.S(a.l.), Ba.S∡, Ba.S, S.N, S.N(a.l.), S.F(a.l.), F.N (a.l.), S.N∡, and S∡, said variants for said facial depth are selected from the group consisting of Ba.N, Ba.S, S.Ptm, Ptm.A, Ba.A, Ba.Ar, Ar.Po, Ba.B, Ba.Po, Ar.Go(a.l.), RI∡, Ar.Go, Go.Po'(a.l.), MPl∡, B.Po'(a.l.), B.Po, Go.Po, and Go∡, said variants for said facial height are selected from the group consisting of N.M, Ba.S, S.N, Ba.N, Ba.Go, Ar.Go, Ba.Ar(−), Go.M, Ba.M, S.Go, Ba.Pns, Ab.Ans, Pal.∡, N.Ans, Ans.$\underline{1}$, M.$\overline{1}$, $\underline{1}/\overline{1}$, Ans.M., said variants for said dentition as they relate to molars are selected from the group consisting of Ba.S, S.Ptm, Ptm.$\underline{6}$, Ba.$\underline{6}$ (Depth), Ba.Ar, Ar.Go, Go.$\overline{6}$, Ba.$\overline{6}$ (Depth), Ba.Po, and $\overline{6}$.Po, said variants for said dentition as they relate to incisors are selected from the group consisting of Ba.$\underline{1}$ (Depth), $\underline{1}$.BaH (Height), $\underline{1}$.BaV∡, Ba.$\overline{1}$ (Depth), $\overline{1}$.MPl (Height), $\overline{1}$.M (Height), $\overline{1}$.BaV∡, MPl∡, and $\underline{1}$.MPl∡, said variants for said profile as they relate to skeletal/soft tissue profile are selected from the group consisting of Facial∡ and Convexity∡ for both the skeletal profile and the soft tissue profile, said variants for said profiles as they relate to the depth segment are selected from the group consisting of N.Ans., N.A, N.$\underline{1}$, N.$\overline{1}$, N.B, N.Po, N$^s$.Nose tip$^s$, N$^s$.A$^s$, N$^s$.UL$^s$, N$^s$.LL$^s$, N$^s$.B$^s$, N$^s$.Po$^s$, N.N$^s$, Ans.Nose tip$^s$, A.Nose tip$^s$, A.A$^s$, $\underline{1}$.UL$^s$, $\overline{1}$.LL$^s$, B.B$^s$, Po.Po$^s$, and said variants for said profile as they relate to height segment are selected from the group consisting of N.M, N.Ans, Ans.$\underline{1}$, M.$\overline{1}$, $\underline{1}\overline{1}$, Ans.M, N$^s$.M$^s$, N$^s$.Nose tip$^s$, Nose tip$^s$.UL$^v$, M$^s$.LL$^v$, UL$^v$.LL$^v$, Nose tip$^s$.M$^s$, N.N$^s$, Ans.Nose tip$^s$, Ans.UL$^v$, $\underline{1}$.UL$^v$, $\overline{1}$.LL$^v$, M.M$^s$, BaH.N, BaH.-Nose tip$^s$, BaH.Ans, BaH.$\underline{1}$, BaH.UL$^v$, BaH.$\overline{1}$, BaH.LL$^v$, BaH.M; and
   (d) storing the results of said summating step.

* * * * *